US006573245B1

(12) United States Patent
Marciani

(10) Patent No.: US 6,573,245 B1
(45) Date of Patent: Jun. 3, 2003

(54) MODIFIED POLYSACCHARIDE ADJUVANT-PROTEIN ANTIGEN CONJUGATES, THE PREPARATION THEREOF AND THE USE THEREOF

(75) Inventor: Dante J. Marciani, Birmingham, AL (US)

(73) Assignee: Galenica Pharmaceuticals, Inc., Birmingham, AL (US)

(*) Notice: Subject to any disclaimer, the term of this patent is extended or adjusted under 35 U.S.C. 154(b) by 0 days.

(21) Appl. No.: 09/301,115

(22) Filed: Apr. 28, 1999

Related U.S. Application Data

(60) Provisional application No. 60/083,106, filed on Apr. 28, 1998.

(51) Int. Cl.[7] .................. A61K 31/70; A61K 39/00
(52) U.S. Cl. .................. 514/25; 514/42; 514/54; 514/55; 514/61; 424/185.1; 424/193.1; 424/194.1
(58) Field of Search .................. 514/25, 42, 54, 514/55, 61; 424/185.1, 193.1, 194.1

(56) References Cited

U.S. PATENT DOCUMENTS

| 3,236,792 A | | 2/1966 | Curtis .................. 260/17.3 |
|---|---|---|---|
| 4,003,792 A | | 1/1977 | Mill et al. .................. 195/63 |
| 4,063,016 A | | 12/1977 | Austin .................. 536/20 |
| 4,356,170 A | | 10/1982 | Jennings et al. .................. 424/92 |
| 4,424,346 A | | 1/1984 | Hall et al. .................. 536/20 |
| 4,613,665 A | | 9/1986 | Larm .................. 536/20 |
| 4,631,211 A | | 12/1986 | Houghten .................. 428/35 |
| 4,693,891 A | | 9/1987 | Collins et al. .................. 424/92 |
| 4,695,624 A | | 9/1987 | Marburg et al. .................. 530/395 |
| 4,698,387 A | | 10/1987 | Schmidt et al. .................. 525/54.1 |
| 4,734,362 A | | 3/1988 | Hung et al. .................. 435/68 |
| 4,739,046 A | | 4/1988 | Di Luzio .................. 536/17 |
| 4,771,127 A | | 9/1988 | Cryz et al. .................. 530/395 |
| 5,032,401 A | | 7/1991 | James et al. .................. 424/426 |
| 5,057,503 A | | 10/1991 | Czop et al. .................. 514/54 |
| 5,110,909 A | | 5/1992 | Dellacherie et al. .................. 530/385 |
| 5,169,840 A | | 12/1992 | Otterlei et al. .................. 514/55 |
| 5,554,386 A | | 9/1996 | Groman et al. .................. 424/488 |
| 5,567,685 A | | 10/1996 | Linden et al. .................. 514/31 |
| 5,583,112 A | | 12/1996 | Kensil et al. .................. 514/25 |
| 5,623,057 A | * | 4/1997 | Marburg et al. .................. 530/404 |
| 5,668,193 A | | 9/1997 | Gouda et al. .................. 523/112 |
| 5,747,475 A | | 5/1998 | Nordquist et al. .................. 514/55 |
| 5,785,975 A | | 7/1998 | Parikh .................. 424/278 |
| 5,807,559 A | * | 9/1998 | Jondal .................. 424/278.1 |
| 5,929,049 A | * | 7/1999 | Singh et al. .................. 514/54 |
| 5,952,454 A | * | 9/1999 | Kovac et al. .................. 528/332 |
| 5,989,552 A | * | 11/1999 | McKenzie et al. .................. 424/185.1 |

FOREIGN PATENT DOCUMENTS

| EP | 0 320 942 A2 | 6/1989 |
|---|---|---|
| EP | 0 326 111 A2 | 8/1989 |
| EP | 0 477 508 A1 | 4/1992 |
| WO | WO 96/20012 | 7/1996 |
| WO | WO 96/40225 | 12/1996 |
| WO | WO 97/33612 | 9/1997 |
| WO | WO 99/17783 | 4/1999 |

OTHER PUBLICATIONS

Ambrosino, D.M., et al., "Effect of *Haemophilus influenzae* Polysaccharide Outer Membrane Protein Complex Conjugate Vaccine on Macrophages," *J. Immunol.* 149:3978–3983 (Dec. 1992).

Cryz Jr., S.J., et al., "*Pseudomonas aeruginosa* Immunotype 5 Polysaccharide–Toxin A Conjugate Vaccine," *Infect. Immun.* 52:161–165 (Apr. 1986).

Cryz Jr., S.J., et al., "*Pseudomonas aeruginosa* Polysaccharide–Tetanus Toxoid Conjugate Vaccine: Safety and Immunogenicity in Humans," *J. Infect. Dis.* 154:682–688 (Oct. 1986).

Cryz Jr., S.J., et al., "Vaccine Potential of *Pseudonomas aeruginosa* O–Polysaccharide–Toxin A Conjugates," *Infect. Immun.* 55:1547–1551 (Jul. 1987).

Cryz Jr., S.J., et al., "Octavalent *Pseudomonas aeruginosa* O–polysaccharide–toxin A congugate vaccine," *Microbial Pathogenesis* 6:75–80 (Jan. 1989).

Good, A.H., et al., "Identification of Carbohydrate Structures That Bind Human Antiporcine Antibodies: Implication for Discordant Xenografting in Humans," *Transplantation Proceedings* 24(2):559–562 (Apr. 1992).

Inman, J.K., "Thymus–Independent Antigens: The Preparation of Covalent, Hapten–Ficoll Conjugates," *J. Immunol.* 114:704–709 (Feb. 1975).

Jiang, W., et al., "The receptor DEC–205 expressed by dendritic cells and thymic epithelial cells is involved in antigen processing," *Nature* 375:151–155 (May 1995).

Kolar, C., et al., "Preparation and Use of Synthetic Blood Group Specific Immunoadsorbents," *Behring Inst. Mitt.* 82:94–103 (1988).

(List continued on next page.)

*Primary Examiner*—Samuel Barts
*Assistant Examiner*—Devesh Khare
(74) *Attorney, Agent, or Firm*—Sterne, Kessler, Goldstein & Fox, P.L.L.C.

(57) ABSTRACT

The present invention is directed to chemical conjugates (herein referred to as polysaccharide adjuvant-antigen conjugates) that have a polysaccharide backbone capable of binding to the cell surface of Antigen Presenting Cells (APCs), to which is covalently attached (a) one or more molecules having a stable carbonyl group (i.e. an aldehyde and ketone group that is capable of reacting with amino groups to form an imine or Schiff base), and (b) one or more polypeptides or peptides that are capable of eliciting an immunogenic response when covalently attached to polysaccharide backbone. Also disclosed are methods for making the conjugates and methods of using the conjugates to enhance the potentiation of an immune response in a mammal. Also disclosed is a method of vaccination, and pharmaceutical and veterinary compositions comprising one or more of the polysaccharide adjuvant-antigen conjugates of the present invention.

31 Claims, No Drawings

OTHER PUBLICATIONS

Lagergard, T., et al., "Synthesis and Immunological Properties of Conjugates Composed of Group B Streptococcus Type III Capsular Polysaccharide Covalently Bound to Tetanus Toxoid," *Infect. Immun.* 58:687–694 (Mar. 1990).

Lett, E., et al., "Immunogenicity of Polysaccharides Conjugated to Peptides Containing T– and B–Cell Epitopes," *Infect. Immun.* 62:785–792 (Mar. 1994).

Lett, E., et al., "Mucosal Immunogenicity of Polysaccharides Conjugated to a Peptide of Multiple–Antigen Peptide Containing T– and B–Cell Epitopes," *Infect. Immun.* 63:2645–2651 (Jul. 1995).

Murata, J.–i., et al., "Synthesis of muramyl dipeptide analogue–glucomannan conjugate and its stimulation activity against macrophage–like cells," *Carbohydrate Polymers* 29:111–118 (Feb. 1996).

Ohya, Y., et al., "Synthesis of a MDP Analogue/Chitin Conjugate That Stimulates Cultured Macrophages," *J. Bioactive & Compatible Polymers* 8:351–364 (Oct. 1993).

Ouchi, T., et al., "Design of D–glucose Analogue of MDP/ CM–Polysaccharide Conjugates Exhibiting Macrophage Activities," in Anaheim, Book of Abstracts, 209th ACS National Meeting, Apr. 2–6, Abstract No. 043, p. Cell (Apr. 1995).

Rioux, S., et al., "Evaluation of Protective Efficacy of an *Actinobacillus pleuropneumoniae* Serotype 1 Lipoplysaccharide–Protein Conjugate in Mice," *Comp. Immun. Microbiol. Infect. Dis.* 20:63–74 (Jan. 1997).

Stahl, P.D., "The manose receptor and other macrophage lectins," *Current Opinion in Immunology* 4:49–52 (Feb. 1992).

Kensil, C.R., et al., "Structure/Function Relationship in Adjuvants from *Quillaja saponaria* Molina," in *Vaccines92: Modern Approaches to New Vaccines Including Prevention of AIDS*, Brown, F., et al., eds., Cold Spring Harbor Laboratory Press, Cold Spring Harbor, NY, pp. 35–40 (1992).

Apostolopoulos, V., et al., "Oxidative/reductive conjugation of mannan to antigen selects for $T_1$ or $T_2$ immune responses," *Proc. Natl. Acad. Sci. USA* 92:10128–10132, National Academy of Sciences (1995).

Apostolopoulos, V., et al., "Cell–mediated immune responses to MUC1 fusion protein coupled to mannan," *Vaccine* 14:930–938, Elsevier Science Ltd. (1996).

Arnon, R., et al., "Antiviral response elicited by a completely synthetic antigen with built–in adjuvanticity," *Proc. natl. Acad. Sci. USA* 77:6769–6772, National Academy of Sciences (1980).

Azuma, I., "Synthetic immunoadjuvants: application to non– specific host stimulation and potentiation of vaccine immunogenicity," *Vaccine* 10:1000–1006, Butterworth–Heinemann Ltd. (1992).

Barreto–Bergter, E. and Gorin, P.A.J., "Structural Chemistry of Polysaccharides from Fungi and Lichens," in*Advances in Carbohydrate Chemistry and Biochemistry*, Tipson, R.S. and Horton, D., eds, Academic Press, Inc., New York, NY, pp. 67–103 (1983).

Berger, L.R. and Reynolds, D.M., "The Chitinase System of a Strain of *Streptomyces griseus*," *Biochim. Biophys. Acta* 29:522–534, Elsevier Publishing Company (1958).

Bohn, J.A. and BeMiller, J.N., "(1→3)–β–D–Glucans as biological response modifiers: a review of structure–functional activity relationships," *Carbohydr. Polym.* 28:3–14, Elsevier Science Ltd. (1995).

Dalsgaard, K., "A Study of the Isolation and Characterization of the Saponin Quil A: Evaluation of its Adjuvant Activity, with a Special Reference to the Application in the Vaccination of Cattle against Foot–and–Mouth Disease," *Acta Vet. Scand.* 69:7–40, Danske Dyrlaegeforenging (1978).

Geysen, H.M., et al., "Use of peptide systhesis to probe viral antigens for epitopes to a resolution of a single amino acid," *Proc. Natl. Acad. Sci. USA* 81:3998–4002, National Academy of Sciences (1984).

Habeeb, A.F.S.A., "Determination of Free Amino Groups in Proteins by Trinitrobenzenesulfonic Acid," *Anal. Biochem.* 14:328–336, Academic Press, Inc. (1966).

Hahn, M.G. and Albersheim, P., "Host–Pathogen Interactions, XIV. Isolation and Partial Characterization of an Elicitor From Yeast Extract," *Plant Physiol.* 62:107–111, American Society of Plant Physiologists (1978).

Houghten, R.A., "General method for the rapid solid–phase synthesis of large numbers of peptides: Specificity of antigen–antibody interaction at the level of individual amino acids," *Proc. Natl. Acad. Sci. USA* 82:5131–5135, National Academy of Sciences (1985).

Janusz, M.J., et al., "Isolation of Soluble Yeast β–Glucans that Inhibit Human Monocyte Phagocytosis Mediated By β–Glucan Receptors," *J. Immunol.* 137:3270–3276, The American Association of Immunologists (1986).

Ohta, M., et al., "Contribution of the mannan O side–chains to the adjuvant action of lipopolysaccharides," *Immunology* 60:503–507, Blackwell Scientific Publications (1987).

Okawa, Y., et al., "Production of anti–peptide specific antibody in mice following immunization with peptides conjugated to mannan," *J. Immunol. Meth.* 149:127–131, Elsevier Science Publishers B.V. (1992).

Rhodes, J., "Covalent chemical events in immune induction: fundamental and therapeutic aspects," *Immunol. Today* 17:436–441, Elsevier Science Ltd. (1996).

Sela, M., "Antigenicity: Some Molecular Aspects," *Science* 166:1365–1374, American Association for the Advancement of Science (1969).

Senju, R. and Okimasu, S., "Studies on Chitin. Part I. On the Glycolation of Chitin and the Chemical Structure of Glycol Chitin," *J. Agr. Chem. Soc. Japan* 23:432–437, The Agricultural Chemical Society of Japan (1950).

Sutcliffe, J.G., et al. "Antibodies That React with Predetermined Sites on Proteins," *Science* 219:660–666, American Association for the Advancement of Science (1983).

van der Bruggen, P., et al., "A Gene Encoding an Antigen Recognized by Cytolytic T Lymphocytes on a Human Melanoma," *Science* 254:1643–1647, American Association for the Advancement of Science (1991).

Vinogradov, E., et al., "Structural analysis of the intact polysaccharide mannan from *Saccharomyces cerevisiae* yeast using $^1$H and $^{13}$C NMR spectroscopy at 750 MHz," *Carbohydr. Res.* 307:177–183, Elsevier Science Ltd. (Feb. 1998).

Wilson, I.A., et al., "The Structure of an Antigenic Determinant in a Protein," *Cell* 37:767–778, MIT Press (1984).

Yamada, H. and Kiyohara, H., "Bioactive Polysaccharides from Chinese Herbal Medicines," *Abs. Chin. Med.*3:104–124, Chinese University of Hong Kong (1989).

Yamada, H., et al., "Structural Characterization and Antitumor Activity of a Pectic Polysaccharide from the Roots of *Angelica acutiloba*," *Planta Medica* 56:182–186, Thieme Medical Publishers, Inc. (1990).

Zheng, B., et al., "Galactose Oxidation in the Design of Immunogenic Vaccines," *Science* 256:1560–1563, American Association for the Advancement of Science (1992).

Database CAplus, Accession No. 1952:48381, English language abstract for Senju, R. and Okimasu, S., attached as documeent AT12.

Dellacherie, E. and Bonneaux, F., "A new approach to aldehydic dextrans," *Polymer Bulletin* 31:145–149, Springer–Verlag (1993).

* cited by examiner

MODIFIED POLYSACCHARIDE ADJUVANT-PROTEIN ANTIGEN CONJUGATES, THE PREPARATION THEREOF AND THE USE THEREOF

CROSS-REFERENCE TO RELATED APPLICATIONS

This application claims the benefit of earlier filed U.S. patent application Ser. No. 60/083,106, filed Apr. 28, 1998, the contents of which are fully incorporated by reference herein.

BACKGROUND OF THE INVENTION

1. Field of the Invention

The present invention is related to polysaccharide derivatives, their preparation and their use in vaccines and immunostimulating compositions. More particularly, the invention is related to antigen-adjuvant conjugates that are derivatives of polysaccharides recognized by antigen presenting cells (APCs) conjugated with an antigen.

2. Related Art

Adjuvants have utility in activating the immune system to increase the efficacy of preventative and therapeutic vaccines. Immunoadjuvants have applications in: (1) the non-specific stimulation of host resistance against infection and cancer, (2) the potentiating of preventative vaccine immunogenicity, and (3) the potentiating of therapeutic vaccine immunogenicity. These adjuvants may preferentially enhance cell-mediated immune responses (T cell responses, delayed hypersensitivity), humoral responses (B cell responses, antibody production), or both. Stimulation of humoral immunity is important for prevention of bacterial infections, some viral infections, as well as in therapy of soft tissue and circulating cancers. Cellular immunity is of major importance for solid tumor cancer therapy and some viral diseases.

After an initial stimulation by a foreign agent or antigen (such as viruses, bacteria, or parasites), the immune system usually recognizes and reacts to the agent with an accelerated response upon re-exposure. This enhanced response forms the basis for the enormous success of vaccination for disease prevention. However, the initial immune response to a foreign antigen requires several days for full response, which is insufficient for protection against infections by highly virulent organisms. A way to achieve a faster protective immune response is by vaccination or immunization with a pathogen, which is usually attenuated or dead. However, in many cases immunization with killed microorganisms or with pure antigens elicits a poor short term immune response with weak or no cell-mediated immunity produced at all. In many cases this poor immune response can be modified by the addition of adjuvants to the antigen preparation. Several polysaccharides (carbohydrate polymers) of mannose (e.g. mannans), β(1,3) glucose (e.g. glucans), β(1,4) acetylated mannose (acemannans), β(1,4) N-acetyl-glucosamine (chitins), and heteropolysaccharides, such as rhamnogalacturonans (pectins), have been shown to stimulate the immune system. Antigen presenting cells (APCs) have specific cell-surface-receptors which recognize and bind the sugar moieties of these and other polysaccharides. Antigen presenting cells (APCs), such as dendritic cells and some macrophages, are responsible for taking up antigens and processing them to small peptides in endolysosomes. Processed antigens are expressed on the surface of APCs in conjunction with class II MHC. Specifically, reactive T cells recognize antigen and class II MHC simultaneously, yielding immune responses that are class II MHC restricted. B cells are stimulated by processed antigens to produce antibodies. These APC surface-receptors (such as the macrophage mannose receptor and its homologous receptor DEC-205 from dendritic cells) are transmembrane proteins that mediate endocytosis and apparently play a role in the process of antigen presentation. (Stahl, P. D., *Current Opinions in Immunology* 4:49 (1992); and Jiang, W. et al., *Nature* 375:151 (1995)). Binding of these polysaccharides to such receptors apparently induces immunostimulation, as shown by the increase in phagocytosis, proliferative responses, release of cytokines, and other activities of the immune system. Because of this immunostimulatory activity, these polysaccharides have been proposed as vaccine adjuvants.

Polysaccharide adjuvants exert an immunomodulating effect by modifying cytokine production, such as upregulating IL-1, and causing a moderate Th1 response. The immune response produced by the Th1 subset of $CD4^+T$ cells induces complement fixing antibodies as well as strong, delayed-type hypersensitivity (DTH) reactions associated with γ-IFN, IL-2 and IL-12. Polysaccharides' effects on the native protein conformation are moderate, preserving the conformational epitopes necessary to elicit a neutralizing antibody response. However, because these adjuvants cannot allow exogenous antigens to be processed via the endogenous pathway, they do not induce a cytotoxic T lymphocyte (CTL) response. Because APCs have cell-surface-receptors specific for certain carbohydrate moieties, the targeting and delivery to these cells of antigens associated with these sugar moieties can be significantly enhanced. Apparently, the role of sugar moieties in the targeting of antigen delivery is not limited to polysaccharide adjuvants. For instance, the modification of quillajasaponin carbohydrate side-chains by periodic acid oxidation results in a loss of their adjuvanticity. Presumably, this results because of the loss of their targeting capacity.

Although the adjuvant properties of certain polysaccharides have been known for some time, their use has been largely limited to research applications. For instance, it has been shown that glucans can induce an anti-tumor response in mice, and have a preventive effect on acute sepsis. These effects are dependent on the glucans' molecular weight and their degree of branching. Mannans are other polysaccharides with adjuvant activity which presumably exert their effect after binding to the macrophage mannose cell-surface-receptor. Recently, it has been shown that conjugation of a protein antigen to mannan under oxidizing conditions resulted in a cell-mediated immune response (Apostolopoulos, V. et al., *Vaccine* 14: 930(1996)). However, protein antigens conjugated to mannans under non-oxidative conditions, i.e. without aldehyde formation, elicited only humoral immunity (Okawa, Y. et al., *J. Immunol. Meth.* 142:127 (1992)) and (Apostolopoulos, V. et al., *Proc. Natl. Acad. Sci. USA*. 92:10128 (1995)). Stimulation of T-cell immunity has also been achieved by generating with galactose oxidase under experimental conditions, aldehydes in the galactosyl residues of cell-surface polysaccharides (Zeng, B., et al., *Science* 256:1560(1992)). However, this immunostimulation was not reproducible (Rhodes, *J. Immunol. Today* 17:436(1996)). These results highlight the problems associated with aldehyde instability and/or the inefficient production of aldehydes by enzymatic oxidation.

Commonly-assigned, co-pending U.S. patent application Ser. No. 09/165,310, filed Oct. 2, 1998, discloses polysaccharide conjugates that comprise (i) a polysaccharide that binds to surface-receptors present on Antigen Presenting Cells (APCs), and (ii) one or more compounds having a stable carbonyl group (i.e. an aldehyde and ketone group that is capable of reacting with amino groups to form an imine or Schiff base) wherein compounds (ii) are attached to the polysaccharide (i) through (iii) a direct covalent bond or covalently via the residue of a bifunctional linker. The conjugates are useful as adjuvants or immunostimulants.

It has been reported that certain protein antigens linked covalently to an adjuvant to form conjugates may have a immunogenicity higher than that of the antigen mixed with the adjuvant. For instance, addition of the adjuvant muramyl dipeptide (MDP) to a synthetic viral antigen resulted in a limited adjuvant effect. However, a covalent conjugate of this antigen with MDP elicited a strong immune response (Arnon et al., *Proc. Natl. Acad. Sci. USA* 77:6769–6772 (1980)). Conjugation of the quillajasaponin adjuvant (QS-21) with a poorly immunogenic protein, lysozyme, resulted in an enhanced immunogenicity (Kensil et al., *Vaccines 92*, Cold Spring Harbor Laboratory, pp. 35–40; and U.S. Pat. No. 5,583,112 (1992)), whereas mixtures of lysozyme with QS-21 failed to elicit an immune response. Recently, it has been reported that when a mucin (MUC1) fusion protein is conjugated to mannan under oxidizing conditions an effective anti-tumor cellular immune response is induced (Apostolopoulos et al., *Vaccine* 14:930–938 (1996)). However, conjugation of the protein to the polysaccharide with cyanogen bromide, via isourea bonds, did not elicit a cellular immune response. The authors indicate that the presence of aldehyde groups, produced by oxidation of the polysaccharide with periodate, was required to elicit T-cell immunity.

Thus, antigens conjugated to certain adjuvants show an enhanced immunogenicity. Furthermore, it is apparent that in some cases these conjugates are capable of eliciting a specific CTL response. Although the mechanism of how a conjugate elicits a CTL response is not known, it is possible that the adjuvant part is responsible for the initial targeting, binding to the surface of antigen presenting cells (APCs), and co-stimulation. Once this binding has taken place, the conjugate can be internalized into the co-stimulated cell's cytosol by endocytosis/pinocytosis, and the antigen processed as an endogenous one. Although, there are reports of the utility of quillajasaponins to form antigen-adjuvant conjugates, their intrinsic toxicity and instability make their use in commercial products difficult. Antigen-adjuvant conjugates of periodic acid-oxidized polysaccharides are non-toxic. However, the inconsistent production of short-lived aldehydes by oxidizing polysaccharide sugar residues makes this approach unsuitable for commercial purposes as well.

Thus, to elicit an enhanced and useful T-cell immune response, such as that needed for clinically-useful viral and cancer vaccines, it would be advantageous to use stable, reproducible and non-toxic antigen-adjuvant conjugates as antigens. The present invention is directed to the preparation of reproducible, stable, and non-toxic antigen-adjuvant conjugates that are capable of targeting and co-stimulating APCs, and their use of such conjugates as vaccine antigens to stimulate T-cell immunity.

SUMMARY OF THE INVENTION

The present invention is directed to chemical conjugates (herein referred to as polysaccharide adjuvant-antigen conjugates) that comprise:

(i) a polysaccharide capable of binding to the cell surface of Antigen Presenting Cells (APCs);

(ii) one or more molecules having a stable carbonyl group (i.e. an aldehyde and ketone group that is capable of reacting with amino groups to form an imine or Schiff base);

(iii) one or more polypeptides or peptides that are capable of eliciting an immunogenic response when covalently attached to polysaccharide backbone (i);

wherein molecules (ii) are attached to the polysaccharide (i) through (iv) a direct covalent bond or covalently via a bifunctional linker in a manner that keeps the stable carbonyl group intact; and wherein said one or more polypeptides or peptides (iii) are attached to the polysaccharide (i) through (v) a direct covalent bond or covalently via a bifunctional linker.

The present invention is directed to enhancing the potentiating of an immune response in a mammal, comprising administering an effective amount of a polysaccharide adjuvant-antigen conjugate of the present invention to enhance the immune response of a mammal to one or more antigens.

The present invention is also directed to a method of vaccination, comprising administering one or more polysaccharide adjuvant-antigen conjugates of the present invention.

The present invention is also directed to pharmaceutical and veterinary compositions comprising one or more of the polysaccharide adjuvant-antigen conjugates of the present invention, and one or more pharmaceutically acceptable diluents, carriers or excipients. These compositions may be employed as immunopotentiators in animals and humans.

The present invention is also directed to vaccines comprising one or more polysaccharide adjuvant-antigen conjugates of the present invention.

DETAILED DESCRIPTION OF THE PREFERRED EMBODIMENTS

The present invention is directed to polysaccharide conjugates, comprising:

(i) a polysaccharide capable of binding the surface of Antigen Presenting Cells (APCs);

(ii) one or more molecules having a stable carbonyl group (i.e. an aldehyde and ketone group that is capable of reacting with amino groups to form an imine or Schiff base);

(iii) one or more polypeptides or peptides that are capable of eliciting an immunogenic response when covalently attached to polysaccharide backbone (i);

wherein molecules (ii) are attached to the polysaccharide (i) through (iv) a direct covalent bond or covalently via the residue of a bifunctional linker in a manner that keeps the stable carbonyl group intact; and wherein said one or more polypeptides or peptides (iii) are attached to the polysaccharide (i) through (v) a direct covalent bond or covalently via the residue of a bifunctional linker.

The compounds having the imine-forming carbonyl group can be an aromatic or non-aromatic cyclic, aromatic or non-aromatic heterocyclic or non-cyclic compounds. Preferably, aromatic or heteroaromatic ketones and aldehydes are employed as (ii).

In order to more clearly explain this aspect of the present invention, polysaccharide conjugates can be represented by the Formula:

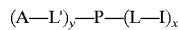

or pharmaceutically acceptable salts thereof, where

P is a polysaccharide that is capable of binding to the cell surface of an Antigen Presenting Cell;

each L' is independently a covalent bond, or a bifunctional linking molecule;

A is a protein or peptide that is capable of eliciting an immunogenic response when covalently attached to a polysaccharide backbone. When y is greater than 1, each A can be the same or different protein or peptide antigen;

each L is independently a covalent bond, or a bifunctional linking molecule;

I is an imine-forming compound. When x is greater than 1, each I can be the same or different imine-forming compound. Preferred imine-forming compounds are aliphatic, aromatic or heteroaromatic compounds having (a) a ketone or aldehyde functionality; and (b) a second functional group that is capable of reacting with a complementary functional group present on said polysaccharide or said bifunctional linking molecule, if present; and x and y are independently greater than or equal to one.

The values of x and y will be determined by the number of reactive groups that are covalently modified on the polysaccharide. A number of factors and strategies will influence the values of x and y as will be more fully detailed herein. Generally, x will be a function of the number of reactive hydroxy, terminal-end hemiacetal and/or carboxy groups that are present on the polysaccharide. Because of the diverse molecular weight distribution of useful polysaccharides (P), the degree of modification as represented by x may be expressed as the number of imine-forming groups introduced per hundred glycosyl residues. Using this convention, the value of x can vary from 1 to more than 100, with a preferred range of from 1 to about 50 imine-forming groups per 100 glycosyl residues. The value of y can vary from 1 to more than 100. Preferably, the value of y can vary from about 1 to about 20, more preferably, about 1 to about 10, and even more preferably 1 to about 5 antigenic groups per 100 glycosyl residues.

The ratio of imine-forming compounds I, and antigenic moieties P, varies broadly depending upon the conjugation strategy employed. Control of this ratio is further described herein.

A free hydroxy, terminal end glycosyl hemiacetal or carboxylic acid group of the polysaccharides is employed to covalently link the polysaccharide P to L or L', or directly to I and/or A. One or more of these reactive groups that are present on the polysaccharide can be first "activated" (as further described herein) to increase the reactivity of these groups, or the polysaccharide can be reacted with an imine-forming compound having an "activated" functional group.

Schemes 6 and 7, appearing prior to the claims, illustrate the structure of the conjugates in more detail. The "protein" exemplified in these schemes can be replaced by any useful immunogenic polypeptide or peptide.

Polysaccharides

Polysaccharides that can be employed to form conjugates of the present invention include any polysaccharide, natural or chemically modified, that binds to cell surface receptors on APCs. For purposes of the present invention, useful polysaccharides comprise a minimum of two saccharides, preferably seven or more saccharides, and are unbranched or branched, and can have a molecular weight of from about 1000 to several million Daltons. Preferred polysaccharides have a molecular weight of from about 1,000 to about 500,000. The polysaccharides may possess chemical modifications as described herein.

The term "Antigen Presenting Cells" or the abbreviation "APCs" for purpose of the present invention mean dendritic cells and macrophages that are responsible for taking up antigens, processing them to small peptides, and expressing them on their surface in conjunction with class II MHC for presentation to T and B cells.

During evolution macrophages and dendritic cells have developed cell surface receptors that recognize the carbohydrate moieties from different microorganisms. These receptors play a critical role in phagocytosis as well as in pinocytosis, two processes that are involved in antigen presentation. Polysaccharides recognized by these cell-surface-receptors would be suitable for the construction of these adjuvants because such polysaccharides provide an effective mechanism for APC targeting. In some cases, carbohydrate sequences from bacterial, fungal, and animal origins are shared by plant polysaccharides. Thus, plant polysaccharides can provide a practical source of starting materials in some instances. Although these adjuvants can be prepared with either soluble or insoluble polysaccharides, the soluble forms are preferred.

The applications of the present disclosure are in no way limited to plant polysaccharides. They can be extended to other carbohydrate-containing compounds from different sources that are recognized by APCs surface receptors. Examples of these other polysaccharides are chitins and dextrans which are of animal and bacterial origin respectively. Examples of suitable carbohydrate-containing compounds are bacterial teichoic acids and their derivatives, bacterial lipopolysaccharides, lipid A, and their derivatives.

Among the preferred polysaccharides that are useful in the present invention are: β-glucans; mannans; pectic polysaccharides; chitin and its derivatives; murein, bacterial fructans, xanthans, bacterial heteropolysaccharides, and fungal pullulan. Also useful are derivatives of these polysaccharides. Useful derivatives include polysaccharide esters; sulfonated, sulfated and phosphorylated polysaccharides; polysaccharide ethers, including carboxymethyl, ethylamino and hydroxy ethers; and cross-linked polysaccharides. These derivatives are more fully described in Roberts, J. F., *Essentials of Carbohydrate Chemistry*, Springer-Verlag, New York (1998), which is fully incorporated-by-reference herein. The most preferred polysaccharides are more fully described below.

β-Glucans: β-Glucans have a backbone chain of (1→3)-linked β-D-glucopyranosyl units which has β-D-glucopyranosyl units attached by (1→6) linkages. They are found in several sources, such as yeast, fungi, algae, and cereals. They have abroad range of molecular weights, i.e. between 5,000 to >500,000, which influence their immunomodulating properties. In general, β-glucans of high molecular weight that are relatively insoluble in water have higher biological activity. However, this lack of solubility has precluded the systemic administration of glucans. Modification of these polysaccharides by introduction of anionic groups, such as phosphate, sulfate, carboxyl, and others, has yielded soluble forms that apparently retain their biological activities. Soluble glucans can be prepared by one of the following procedures: i) isolation from yeast extracts (Hahn & Albersheim, 1978, *Plant Physiol*. 66:107), ii) sonication of glucan particles (Januz et al. 1986, *J. Immunol*. 137:327, and iii) introduction of anionic groups to insoluble glucans by sulfonylation, phosphorylation, carboxymethylation, or sulfation ((Bohn & BrMiller, 1995, *Carbohydr. Polym*. 28:3), (Di Luzio, U.S. Pat. No. 4,739,046, 4/1988)). In β-glucans the only reducing glucosyl residue (linked at position 3) is located at the terminus of the backbone chain of (1→3)-linked β-D-glucosyl residues. The glucosyl residues attached by (1→6) linkages to the backbone chain do not have a free reducing group. The smallest fragment that binds to the monocyte glucan receptor is a (1→3)linked β-glucanoheptasaccharide. However, this oligosaccharide does not have immunostimulating activity.

Mannans: Mannans are linear or branched polysaccharides formed exclusively of mannose. Mannans are found in plants, mold, bacteria and other organisms. In certain plants, linear mannans consist of β-(1→4) linked mannosyl residues, whereas in some yeasts, the mannosyl residues are linked by α-(1→2) and α-(1→6) linkages. In the branched mannans from *Saccharomyces cerevisiae* (baker's yeast), the mannan consists of a α-(1→6) linked mannopyranosyl backbone structure substituted on the O-2 atoms by side-chains of α-D-mannopyranosyl, α-D-mannopyranosyl-α-(1→2)-α-D-mannopyranosyl and α-D-mannopyranosyl α-(1→3)-α-D-mannopyranosyl-α-(1→2)-α-D-mannopyranosyl. In addition, the *S. cerevisiae* mannan can also be phosphorylated (Barreto-Bergter and P. A. Gorin, *Adv. Carbohydr. Chem. Biochem.* 41:67 (1983), Vinogradov, E., et al., *Carbohydr. Res.* 307:177 (1998)). Although the ability of *S. cerevisiae* mannans to stimulate cell-mediated immunity is questionable, they enhance the action of lipopolysaccharides in stimulating T-cell responses (Ohta, M., et al., *Immunology* 60:503 (1987)). It appears that mannans can exert their immunostimulatory effects by binding to the macrophage mannose-binding cell-surface receptors. A derivative of β-mannans, the acetylated β-(1→4) polymannose, appears to stimulate the immune system in a manner similar to mannans.

Pectic polysaccharides: Several pectic polysaccharides are anti-complementary, and they may have different degrees of immunopotentiators activity (Yamada, H., et al., *Planta Medica* 56:182 (1990)). Oxidation of these polysaccharides with periodic acid results in a loss of anticomplementary activity on the classical pathway, but increased activity on the alternative pathway (Yamada, H. and Kiyohara, H., *Abstracts of Chinese Medicine* 3(1): 104 (1989)). The polysaccharides showing some immunopotentiating activity and thus, being recognized by cell surface-receptors can be grouped broadly into homogalacturonans, rhamnogalacturonans, arabans, galactans, and arabinogalactans. However, not all of these compounds would have biological activity. In many cases, the activity would be dependent on structure, molecular weight, aggregation state, and other parameters. In general, pectic polysaccharides are a group of sugar polymers associated with 1,4-linked α-D-galactosyluronic acid residues. These polysaccharides may have several branched oligosaccharides linked to the backbone's galactosyluronic acid residues. From previous studies with saponins and other polysaccharides, branched oligosaccharides appear to be relevant for adjuvanticity.

2-Acetamido glucans: chitin, murein and their derivatives: Chitin is a linear N-acetyl-D-glucosamine (NAG) polymer linked by β-(1→4) linkages that has about 16 percent of its NAG residues deacetylated. It is widely distributed in nature: it has been found in the exoskeleton of arthropods and in the cell walls of fungi. This polysaccharide has chains that form extensive intermolecular hydrogen bonds, making it insoluble in water and in different organic solvents. Removal of chitin's N-acetyl groups by strong alkali treatment yields chitosan, a β-(1→4) poly-D-glucosamine water-soluble polycation. Chitosan with 70% of its N-acetyl groups removed (deacetylated chitin), shows a significant immunostimulating activity (Azuma, I., *Vaccine* 10: 1000 (1992)). To avoid the limitations imposed by its insolubility, several chitin derivatives that are more soluble in water have been developed, such as glycol chitin (Senzyu, K., et al., *J Japan, Agri. Chem. Soc.*, 23:432 (1950)) and carboxymethyl chitin that may also have immune stimulatory properties. Water-soluble alcohol-insoluble chitodextrins composed of heptamers or larger NAG oligosaccharides have been prepared by limited acid hydrolysis (Berger, L. R., et al., *Biochim. Biophys. Acta* 29:522 (1958)). Murein, the major component of bacterial cell walls, is a polysaccharide made of β-(1→4) linked NAG, with one of the NAG units substituted at C-3 with an O-lactic acid group by an ether linkage to yield N-acetyl-D-muramic acid (NAM) forming the repeating sequence NAG-NAM. Because of the lactic acid residues, isolated mureins are water-soluble. In the bacterial cell wall, murein is attached to certain peptides to form a cross-linked peptido-glycan. Because of their structural similarities, chitin and murein are recognized by the enzyme lysozyme, and apparently also by receptors on the macrophage's cell surface. These structural similarities, which are also present in glycol chitin, may explain the immunostimulatory properties of chitin and some of its derivatives.

Molecules Having a Stable Carbonyl Group (Imine-Forming Compounds)

The second element of the conjugates of the present invention is one or more molecules having a stable carbonyl group (i.e., an aldehyde and ketone group) that is capable of reacting with an amino group to form an imine or Schiff base. The compounds having the imine-forming carbonyl group can be an aromatic or non-aromatic (saturated or partially unsaturated) carbocycle, aromatic or non-aromatic (saturated or partially unsaturated) heterocycle or a non-cyclic, aliphatic compound o0 that may have one or more unsaturated bonds. In addition, the compounds have a functional group that allows for covalent attachment to a polysaccharide, either through a direct bond, or via a bifunctional linker.

There is evidence that certain aromatic compounds with carbonyl groups are very effective in forming imines or Schiff bases upon reaction with amino groups on certain Th-cell surface receptor(s). Because carbonyl groups attached to aromatic compounds are more stable (whereas aliphatic aldehydes are generally unstable), their derivatives typically have a longer shelf life. Furthermore, the hydrophobic character of the cyclic compounds carrying the carbonyl groups will strengthen the interactions between cell surface receptors and the polysaccharide conjugates. Consequently, the compounds to be used to modify the polysaccharides are preferably aryl or heteroaryl aldehydes or ketones. To facilitate the access of these compounds to the amino groups on T-cells, it is more preferred that they also have some hydrophilic characteristics.

Compounds that embody some degree of all of the aforementioned properties are preferred agents for modifying the polysaccharides. Preferred compounds include mono- and di-substituted $C_{6-10}$ arylaldehydes and $C_{6-10}$ aryl($C_{1-4}$)alkylaldehydes, compounds comprising an aryl group, such as phenyl or naphthyl and include a formyl or formyl($C_{1-4}$)alkyl substituent. Preferably, these compounds further include one or two additional substituents such as halo, hydroxy, $C_{1-4}$alkyl, $C_{1-4}$hydroxyalkyl, $C_{1-4}$alkoxy, trifluoromethyl, or benzyloxy. Suitable examples include benzaldehyde and naphthaldehyde, substituted by one or two of hydroxy and halo. Examples include 2,3-dihydroxybenzaldehyde, 2,4-dihydroxybenzaldehyde, 2,5-dihydroxybenzaldehyde, 3,4-dihydroxybenzaldehyde, 5-chloro-2-hydroxybenzaldehyde, vanillin, ethyl vanillin, naringenin, 3-hydroxybenzaldehyde, 4-hydroxybenzaldehyde, and 4-hydroxyphenylacetaldehyde. A second preferred group is hydroxy substituted $C_{1-4}$alkyl($C_{6-10}$)aryl ketones, such as 2-hydroxyacetophenone, 3-hydroxyacetophenone, and 4-hydroxyacetophenone, and hydroxy substituted aryl ketones such as 6-hydroxy-1,2-naphthoquinone. A third preferred group includes heteroaryl aldehydes and ketones. Useful heteroaryl groups are thiophene, furan, benzothiophene, benzofuran, pyridine, quinoline, pyridazine, pyrimidine, pyrazole, imidazole, 1,2,3-triazole, 1,2,4-triazole, isoxazole, and oxazole, each having a keto, formyl or formyl($C_{1-4}$) substituent, and preferably including an additional halo or hydroxy substituent, if these can be accommodated by available ring carbon atoms. Preferably furanyl, pyridyl, and indolylaldehydes and ketones are useful heteroaryl cores. Examples of useful include pyridoxal, 2-thiophenecarboxaldehyde, and 3-thiophenecarboxaldehyde.

Another relatively stable group of cyclic compounds that contain imine-forming carbonyl groups are triterpenoids and steroids having a keto, formyl, or formylalkyl substitution. Examples include androsterone, formyldienolone, progesterone, prednisolone, quillaic acid, and other derivatives.

Also useful as compounds that contain imine-forming carbonyl groups are aliphatic aldehydes and ketones, such as $C_{4-10}$ alkylaldehydes, $C_{4-10}$ alkenylaldehydes, $C_{4-10}$ alkylketones and $C_{4-10}$ alkenylketones, preferably substituted by one or two of amino, hydroxy or a combination thereof.

Bifunctional Linkers—L and L'

Bifunctional linkers are well known in the art for various applications. A number of bifunctional linkers can be employed to form an attachment between a suitable polysaccharide and a suitable imine-forming compound. "Residue of a bifunctional linker" refers to the structure that links a stable carbonyl compound to the polysaccharide after the terminal ends of the bifunctional linker have covalently bonded to said compound and said polysaccharide.

Non-limiting examples of linker groups that can be used to link the stable carbonyl-containing compound to the polysaccharide are alkylene diamines ($H_2N$—$(CH_2)_r$—$NH_2$), where r is from 2 to 12; aminoalcohols (HO—$(CH_2)_r$—$NH_2$), where r is from 2 to 12; aminothiols (HS—$(CH_2)_r$—$NH_2$), where r is from 2 to 12; amino acids that are optionally carboxy-protected; ethylene and polyethylene glycols (H—(O—$CH_2$—$CH_2)_n$—OH, where n is 1–4). Suitable bifunctional diamine compounds include ethylenediamine, 1,3-propanediamine, 1,4-butanediamine, spermidine, 2,4-diaminobutyric acid, lysine, 3,3'-diaminodipropylamine, diaminopropionic acid, N-(2-aminoethyl)-1,3-propanediamine, 2-(4-aminophenyl) ethylamine, and similar compounds.

When a carboxyl group of the polysaccharide is employed as the conjugating group, one or more amino acids can be employed as the bifunctional linker molecule. Thus, an amino acid such as β-alanine, γ-aminobutyric acid or cysteine, or an oligopeptide, such as di- or tri- alanine can be employed as a suitable linking molecule.

Preferred bifunctional linking groups include:
—NH—$(CH_2)_r$—NH—, where r is from 2–5,
—O—$(CH_2)_r$—NH—, where r is from 2–5,
—NH—$CH_2$—C(O)—,
—O—$CH_2$—$CH_2$—O—$CH_2$—$CH_2$—O—,
—NH—NH—C(O)—$CH_2$—,
—NH—C($CH_3$)$_2$C(O)—,
—S—$(CH_2)_r$—C(O)—, where r is from 1–5,
—S—$(CH_2)_r$—NH—, where r is from 2–5,
—S—$(CH_2)_r$—O—, where r is from 1–5,
—S—$(CH_2)$—CH($NH_2$)—C(O)—,
—S—$(CH_2)$—CH(COOH)—NH—,
—O—$CH_2$—CH(OH)—$CH_2$—S—CH($CO_2H$)—NH—,
—O—$CH_2$—CH(OH)—$CH_2$—S—CH($NH_2$)—C(O)—,
—O—$CH_2$—CH(OH)—$CH_2$—S—$CH_2$—$CH_2$—NH—,
—S—$CH_2$—C(O)—NH—$CH_2$—$CH_2$—NH—, and
—NH—O—C(O)—$CH_2$—$CH_2$—O—P($O_2H$)—.

Protein antigens can be conjugated to imine-forming carbonyl containing polysaccharide adjuvants by their side chains, such as amino, carboxyl, sulfhydryl, imidazole, and phenolic groups. Because conformational integrity of the protein antigen is not a requirement for induction of CTL response, the conjugation procedures can be carried-out under denaturing conditions. To minimize cross-linking between the adjuvant and the antigen, the number of reactive groups per mole of either (or both) antigen or adjuvant should be limited to a small number, preferentially less than 5 per molecule. Under these conditions, the conjugates formed will be prevalently of an antigen/adjuvant composition of ~1:1, without extensive cross-linking.

A terminal or ε-amino group of a protein antigen can be linked covalently to polysaccharides by several procedures. If needed, the number of amino groups available for conjugation may be reduced by reversible trifluoroacetylation, or N-acylation with acid anhydrides (i.e., maleic, citraconic, and others), followed by controlled deacylation (see Glazer, A. N., et al., "Chemical Modification of Proteins," in *Laboratory Techniques in Biochemistry and Molecular Biology*, Work and Work, eds., American Elsevier, New York (1975).

Sulfhydryl groups are highly reactive groups with a limited distribution in proteins. These characteristics make them suitable for conjugation of protein antigens to carbonyl-containing polysaccharides. Cross-linking of protein antigens to an aminated-polysaccharide derivatized with carbonyl compounds can be performed with hetero-bifunctional cross-linkers, such as succinimidyl 4-(p-maleimidophenyl)butyrate (SMPB), 4-(4-N-maleimidophenyl)butyric acid hydrazide hydrochloride (MPBH), maleimidobenzoyl-N-hydroxysuccinimide ester (MBS), and others (Pierce). See Scheme 7. In general, these cross-linking agents react first with an amino or a carbonyl group from the polysaccharide, and subsequently with a sulfhydryl group from the protein antigen. The linkage formed by these agents are non-cleavable, and frequently poorly immunogenic.

Additional non-limiting examples of linker groups that can be used to link antigens to the polysaccharide are alkylene diamines ($NH_2$—$(CH_2)_n$—$NH_2$), where n is from 2 to 12; aminoalcohols (HO—$(CH_2)_r$—$NH_2$), where r is from 2 to 12; and amino acids that are optionally carboxy-protected; ethylene and polyethylene glycols (H—(O—$CH_2$—$CH_2)_n$—OH, where n is 1–4) as described above.

Antigenic Polypeptides and Peptides

The conjugates of the present invention can be utilized to enhance the immune response to one or more antigens. Antigens from a variety of pathogenic agents can be employed to form the conjugates of the present invention. Typical antigens suitable for the immune-response provoking conjugates of the present invention include antigens derived from any of the following:

viruses, such as influenza, feline leukemia virus, feline immunodeficiency virus, HIV-1, HIV-2, rabies, measles, hepatitis B, hoof and mouth disease, papilloma virus, cytomegalovirus, herpes simplex, hepatitis A, hepatitis C, HTLV-1 and HTLV-2;

bacteria, such as the ethiological agents of anthrax, leprosy, tuberculosis, diphtheria, Lyme disease, syphilis, typhoid fever, and gonorrhea;

protozoans, such as *Babeosis bovis*, Plasmodium, Leishmania spp. *Toxoplasma gondii*, and *Trypanosoma cruzi*;

fungi, such as Aspergillus sp., *Candida albicans, Cryptococcus neoformans*, and *Histoplasma capsulatum*; and tumor antigens, such as carcinoembryonic antigen, prostate-specific membrane antigen, prostate specific antigen, protein MZ2-E, polymorphic epithelial mucin (PEM), folate-binding-protein LK26, truncated epidermal growth factor receptor (EGRF), Thomsen-Friedenreich (T) antigen, GM-2 and GD-2 gangliosides.

The antigen can be a protein, peptide, polysaccharide or oligosaccharide (free or conjugated to a protein carrier), or mixtures thereof. The proteins and peptides may be purified from a natural source, synthesized by means of solid phase synthesis, or may be obtained means of recombinant genetics. The polysaccharides and oligosaccharides may be isolated from a natural source, or may be synthesized using enzymatic procedures and/or organic synthesis approaches.

As used herein, the phrase "pathogenic agent" means an agent which causes a disease state or affliction in an animal. Included within this definition, for examples, are bacteria, protozoans, fungi, viruses and metazoan parasites which either produce a disease state or render an animal infected with such an organism susceptible to a disease state (e.g., a secondary infection).

As used herein, the term "organism" means any living biological system, including viruses, regardless of whether it is a pathogenic agent.

As used herein, the term "antigen" means a substance that has the ability to induce a specific immune response. For purposes of the present invention, the term "antigen" is used interchangeably with immunogen.

An "immunogenic epitope" is defined as a part of a protein that elicits an antibody response when the whole protein or polypeptide is the immunogen. These immunogenic epitopes are believed to be confined to a few loci on the molecule. On the other hand, a region of a protein molecule to which an antibody can bind is defined as an "antigenic determinant" or "antigenic epitope." The number of immunogenic epitopes of a protein generally is less than the number of antigenic epitopes. See, for instance, Geysen et al., *Proc. Natl. Acad. Sci. USA* 81:3998–4002 (1983).

Additional definitions are provided throughout the specification.

Conjugates of the present invention can include one or more bacterial antigens from a particular bacteria, including: *Helicobacter pylori, Chlamydia pneumoniae, Chlamydia trachomatis, Ureaplasma urealyticum, Mycoplasma pneumoniae*, Staphylococcus spp., *Staphylococcus aureus*, Streptococcus spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa*, Campylobacter spp., *Campylobacter jejuni*, Clostridium spp., *Clostridium difficile*, Mycobacterium spp., *Mycobacterium tuberculosis*, Treponema spp., Borrelia spp., *Borrelia burgdorferi*, Leptospira spp., *Hemophilus ducreyi, Corynebacterium diphtheria, Bordetella pertussis, Bordetella parapertussis, Bordetella bronchiseptica, hemophilus influenza, Escherichia coli*, Shigella spp., Erlichia spp., and Rickettsia spp.

Bacterial antigens can be native, recombinant or synthetic. Such bacterial antigens include, but are not limited to, selectins or lectins from bacteria that bind to carbohydrate determinants present on cell surfaces; and bacteria receptors for proteins, such as fibronectin, laminin, and collagens.

Conjugates of the present invention can include one or more one or more antigens from a particular virus, including: Influenza viruses, Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease.

Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses.

Conjugates of the present invention can include one or more tumor associated antigens. Tumor associated antigens can be native, recombinant or synthetic. Such tumor associated antigens include, but are not limited to, protein MZ2-E, polymorphic epithelial mucin, folate-binding protein LK26, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, MUC-1 and peptide fragments thereof, CA 125, 15-3,19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, truncated epidermal growth factor receptor (EGFR), and chimeric protein $p210^{BCR-ABL}$.

Useful peptides or polypeptides may comprise an epitope-bearing portion of a polypeptide known to elicit an antibody and/or an antigen-specific cytotoxic T lymphocyte (CTL) response when the whole polypeptide is administered to an animal. The epitope of this polypeptide portion is an immunogenic or antigenic epitope of the polypeptide. An "immunogenic epitope" is defined as a part of a protein that elicits an antibody and/or an antigen-specific cytotoxic T lymphocyte (CTL) response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., "Antibodies that react with predetermined sites on proteins", *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides that can be employed to form conjugates of the invention are therefore useful to raise antibodies, including monoclonal antibodies, that bind specifically to a particular polypeptide. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about at least about 15 to about 30 amino acids contained within the amino acid sequence of a particular polypeptide.

Epitopes recognized by the T-cell receptors on CTLs may be different from those seen by antibodies. Usually, CTLs recognize peptides (derived from proteins enzymatically degraded in the cytosol compartment) which are bound to MHC class I molecules and exposed on the cell surface. These CTL-recognized peptides bind selectively to MHC class I molecules according to MHC allele-specific sequence motifs. These peptides can be identified by expression cloning. See van der Bruggen, P., et al., *Science* 245:1643 (1991). Alternatively, CTL-recognized peptides can be identified by induction of CTLs by in vitro stimulation with peptides derived from the protein antigen used for immunization. The particular CTL-recognized epitope-bearing peptides and polypeptides of the invention preferably are sequences of at least six amino acids, and more preferably between 7 to 20 amino acids. These peptides can be used to form conjugates of the invention and are useful to raise antibodies as well as antigen-specific CTLs or T-cell immunity.

Epitope-bearing peptides and polypeptides may be produced by any conventional means. Houghten, R. A., "General method for the rapid solid-phase synthesis of large numbers of peptides: specificity of antigen-antibody interaction at the level of individual amino acids", *Proc. Natl. Acad. Sci. USA* 82:5131–5135 (1985). This "Simultaneous Multiple Peptide Synthesis (SMPS)" process is further described in U.S. Pat. No. 4,631,211 to Houghten et al. (1986).

Preferred combinations of polysaccharide, imine-forming compound, linkers and ratios for each, may include but are not limited to:

| Polysaccharide (P) | imine-forming compounds (I) | linker (L) | L/P* | I-P* |
|---|---|---|---|---|
| Glucans | 4-hydroxybenzaldehyde | —NH—$(CH_2)_n$—NH—C(O)— | 5-30 | 5-20 |
| Glucans | 4,6-dioxoheptanoic acid | —C(O)—NH—$(CH_2)_n$—NH— | 5-30 | 5-20 |
| Glucans | pyridoxal 5-phosphate | —NH—O—C(O)—$(CH_2)$—C—O— | 5-30 | 5-20 |
| Glucans | 2,4-dihydroxybenzaldehyde | —NH—$(CH_2)_n$—NH—C(O)— | 5-30 | 5-20 |
| Glucans | pyridoxal 5-phosphate | —NH—$(CH_2)_n$—NH—C(O)— | 5-30 | 5-20 |
| Glucans | 2-thiophenecarboxaldehyde | —C(O)—NH—$(CH_2)_n$—NH— | 5-30 | 5-20 |
| Glucans | 3-thiophenecarboxaldehyde | —NH—O—C(O)—$(CH_2)$—C—O— | 5-30 | 5-20 |
| Mannans | 4-hydroxybenzaldehyde | —NH—$(CH_2)_n$—NH—C(O)— | 5-30 | 5-20 |
| Mannans | 4,6-dioxoheptanoic acid | —C(O)—NH—$(CH_2)_n$—NH— | 5-30 | 5-20 |
| Mannans | pyridoxal 5-phosphate | —NH—O—C(O)—$(CH_2)$—C—O— | 5-30 | 5-20 |
| Mannans | 2,4-dihydroxybenzaldehyde | —NH—$(CH_2)_n$—NH—C(O)— | 5-30 | 5-20 |
| Mannans | pyridoxal 5-phosphate | —NH—$(CH_2)_n$—NH—C(O)— | 5-30 | 5-20 |
| Mannans | 2-thiophenecarboxaldehyde | —C(O)—NH—$(CH_2)_N$—NH— | 5-30 | 5-20 |
| Mannans | 3-thiophenecarboxaldehyde | —NH—O—C(O)—$(CH_2)$—C—O— | 5-30 | 5-20 |
| Pectic Polysaccharides | 4-hydroxybenzaldehyde | —NH—$(CH_2)_n$—NH—(O)— | 5-30 | 5-20 |
| Pectic Polysaccharides | pyridoxal 5-phosphate | —NH—$(CH_2)_n$—NH—C(O)— | 5-30 | 5-20 |
| Pectic Polysaccharides | 2-thiophenecarboxaldehyde | —C(O)—NH—$(CH_2)_n$—NH— | 5-30 | 5-20 |
| Pectic Polysaccharides | 3-thiophenecarboxaldehyde | —NH—O—C(O)—$(CH_2)$—C—O— | 5-30 | 5-20 |
| Murein | 4-hydroxybenzaldehyde | —$CH_2$—CHOH—$(CH_2)$—O— $(CH_2)_n$—O—$CH_2$—CHOH—$CH_2$— | 5-30 | 5-20 |
| Murein | 4,6-dioxoheptanoic acid | —C(O)—$(CH_2)_n$—NH— | 5-30 | 5-20 |
| Murein | 2,4-dihydroxybenzaldehyde | —$CH_2$—CHOH—$CH_2$— | 5-30 | 5-20 |
| Murein | pyridoxal 5-phosphate | —NH—$(CH_2)_n$—NH—C(O)— | 5-30 | 5-20 |
| Murein | 2-thiophenecarboxaldehyde | —C(O)—NH—$(CH_2)_n$—NH— | 5-30 | 5-20 |
| Murein | 3-thiophenecarboxaldehyde | —NH—O—C(O)—$(CH_2)$—C—(O)— | 5-30 | 5-20 |
| Glycol chitin | pyridoxal 5-phosphate | —O—C(O)—$(CH_2)$—C—O— | 5-30 | 5-20 |
| Glycol chitin | pyridoxal 5-phosphate | —NH—$(CH_2)_n$—NH—C(O)— | 5-30 | 5-20 |
| Glycol chitin | 2-thiophenecarboxaldehyde | —C(O)—NH—$(CH_2)_n$—NH— | 5-30 | 5-20 |
| Glycol chitin | 3-thiophenecarboxaldehyde | —NH—O—C(O)—$(CH_2)$—C—(O)— | 5-30 | 5-20 |

*I/P and L/P ratios are expressed as I or L molecules incorporated per 100 carbohydrate residues n = 1 to 8.

Preparation of Polysaccharide Adjuvant-Antigen Conjugates

The present invention is also directed to processes for the preparation of polysaccharide adjuvant-antigen conjugates of the present invention. Integrity of the structure of carbohydrate chains is critical for their adjuvanticity. Apparently, the recognition of the carbohydrate moieties by APCs surface-receptors is essential for targeting of the cells as well as to exert their immunostimulatory effects. The adjuvant activity of triterpene saponins also requires an aldehyde group in the triterpenoid moiety. It has also been recently shown that small organic molecules capable of forming imines or Schiff-bases can provide a co-stimulatory signal to T-cells, thus obviating the need for their stimulation by the B7-1 receptor present on APCs. Addition of (i) a cyclic or heterocyclic aromatic compound, or a cyclic or acyclic aliphatic compound having imine-forming carbonyl groups, to (ii) certain polysaccharides recognized and bound by APCs results in products with superior adjuvant properties.

Conjugates of the present invention can be formed by attaching imine-forming compounds and antigenic proteins or peptides to a polysaccharide, either separately or in a single step. To obtain a homogeneous product, as opposed to complex mixtures, imine-forming compounds and the antigenic moieties are separately added to a polysaccharide backbone. In instances where mixtures can be tolerated, for example animal vaccines, less control of the order of addition and reaction conditions is necessary.

A suitable adjuvant for preparation of the conjugates possesses targeting capacity, i.e., recognizes and binds a receptor on the APCs, as well as co-stimulatory activity via an imine-forming carbonyl group. In addition, it possesses reactive groups capable of forming covalent bonds with protein antigens. Certain polysaccharides (i.e., glucans, mannans, chitins, pectins, and others) which are modified to incorporate imine-forming carbonyl groups, fulfill these requirements.

I. Preparation of Modified Polysaccharide Adjuvants Containing Aldehyde Carrying Groups Several immune-stimulating polysaccharides, such as glucans and mannans, comprise either glucosyl or mannosyl residues. The functional groups available for chemical modifications in these sugars are largely hydroxyl groups (—OH) with limited reactivity. Although, one could assume that each —OH group would have the same probability of reacting as the rest, it is possible that structural constraints on —OH group reactivity could favor the production of certain dominant products under limiting reaction conditions. In addition, these polysaccharides may also have one terminal reducing glycosyl residue per linear polymer chain. The limited number of terminal reducing sugars in glucans, mannans, and other polysaccharides, provides a highly specific site for addition of new chemical groups, particularly in oligosaccharides having about 3 to 50 glycosyl residues.

The chemical modifications described here can be used with soluble or insoluble glucans, mannans, and other polysaccharides obtained from different organisms. However, these polysaccharides and the chemical modifications thereof are provided only as examples, not as limitations, of the synthetic procedures available. Because the role of the carbohydrate moieties in these new adjuvants is the targeting of APCs, the useful molecular weight range can be very broad, i.e., from a few hundred to several millions. In the present invention, soluble oligo- and polysaccharides of molecular weights ranging from 1,000 to several 100,000s are preferred.

a) Addition of imine-forming compounds to 1,3-glucans and mannans via their terminal-end glucosyl hemiacetals by reductive amination The reducing terminus of oligosaccharides provides a selective and convenient site for the direct covalent attachment of molecules with amino groups, such as bifunctional diamine compounds. The reductive amination procedure involves reacting the terminal reducing glycosyl residue(s) in the oligosaccharide (or polysaccharide) with a compound carrying one or more primary amino groups in the presence of sodium cyanoborohydride. The cyanoborohydride anion selectively reduces the imine or Schiff base formed by an aldehyde or ketone and an amine. Since the terminal glycosyl hemiacetals are in their formyl or open form for only a brief period of time, the reaction may proceed at very low rate. Scheme 1 illustrates the addition of imine-forming compounds to the polysaccharide carried out as a two-step procedure. The procedure is summarized as follows.

Step 1. Dissolve the glucan/mannan oligosaccharide (or polysaccharide) in an appropriate solvent, such as aqueous acetonitrile, dimethylformamide (DMF), pyridine, or mixtures of the same containing a tertiary amine buffer, at about pH 9; and add a suitable diamine compound in the same solvent. Adjust the final pH to about 9.0. Suitable bifunctional diamine compounds are spermidine, ethylenediamine, 1,4 butanediamine, 2,4-diaminobutyric acid, diaminopropionic acid, lysine, 5-hydroxy-lysine, N-(2-aminoethyl)-1,3-propanediamine, and similar compounds. To avoid cross-linking via the diamine linker, the diamine compound should be present in about a 6 to 10-fold excess over the molar equivalent of free aldehyde groups in the carbohydrate (i.e., one free aldehyde per linear carbohydrate polymer chain). To this solution add the cyanoborohydride dissolved in aqueous 50% acetonitrile, and allow to react at about 40° C. with gentle stirring for several days. The amount of amine compound incorporated in the polysaccharide will be a function of the reaction time, as well as the reaction conditions, and the polysaccharide preparation. Determine the amount of diamine compound incorporated daily with trinitrobenzenesulfonic acid (Habeeb, AFSA *Anal. Biochem.* 14:328 (1966)), to establish the time required to reach a specified diamine incorporation level. The modified aminated glucan/mannan (containing ~1 mole of diamine spacer per polysaccharide linear chain) can be recovered by precipitation with 7 volumes of ethanol, or other suitable solvent, for 24 hours at 4° C. Wash the precipitate on filter paper with ethanol. Dissolve the material in water (if needed bring the pH to between about 4 and about 5 with acetic acid) and lyophilize.

Step 2. Aromatic cyclic or heterocyclic compounds having an imine-forming carbonyl group, and hydroxyl groups (preferably one), such as vanillin, ethyl vanillin, naringenin, pyridoxal, 4-hydroxybenzaldehyde, 2,4-dihydroxybenzaldehyde, and other similar compounds are preferred for addition to the aminated polysaccharides. However, other compounds having carbonyl groups and —OH groups, such as steroid triterpenoid derivatives, and aliphatic aldehydes or ketones, can also be used.

Ten mmoles (1.6 gm) of CDI or N,N'-carbonyldiimidazole dissolved in 10 ml of anhydrous dioxane, acetone, or pyridine, are added in small aliquots with stirring to 10 mmoles of either 5-chloro-2-hydroxybenzaldehyde (1.6 gm), vanillin (1.5 gm), 4-hydroxybenzaldehyde (1.2 gm), or pyridoxal phosphate (2.47 gm), dissolved in 10 ml of dioxane, acetone, or pyridine. Let the reaction proceed for 6–8 hours at about 35–45° C. with mixing. Protect from atmospheric moisture.

The reaction products are: a highly reactive intermediate imidazole-carbamate which is formed with the —OH from the aromatic aldehyde derivatives, plus imidazole. This reaction mixture can be added to the aminated polysaccharides without prior isolation of the intermediate imidazole carbamate which would couple with the modified polysaccharide amino groups to yield stable carbamate linkages. (Imidazole carbamate derivatives can be isolated by procedures such as chromatography, differential extractions, and others).

Reactions between the polysaccharide —OH groups and the imidazole carbamate intermediate can be minimized by allowing the coupling reaction to take place in the presence of amounts of polysaccharide-bound amine which are equimolar or lower than the imidazole carbamate groups. Determine the amount of amino groups in the aminated polysaccharide with TNBS, or for oligosaccharides estimate it from the average molecular weight of the carbohydrate polymer assuming a single terminal reducing sugar per chain. Dissolve the aminated glucan or mannan in a suitable anhydrous organic solvent, such as dimethylsulfoxide (DMSO), dioxane, or pyridine, and adjust the pH to about 9.5–10 with triethylamine. Add an aliquot of the carbamate intermediate containing an amount lower than the amino groups of the polysaccharide preparation, and let the reaction proceed for 12 to 18 hours at 40° C. protected from moisture. (Use of a carbamate intermediate concentration lower than that of —$NH_2$ groups, would also assure the presence of some free —$NH_2$ groups to conjugate a protein antigen). Add about 6–8 volumes of cold ethanol to the reaction and let stand at about 4° C. for 24 hours to precipitate the polysaccharide-aromatic aldehyde derivative. Redissolve the modified polysaccharide in water, and precipitate again with 6–8 volumes of ethanol or other suitable solvent. Determine the coupling efficacy from the residual amino groups, or from the number of aromatic groups in the preparation as determined from UV absorbance measurements at 260–280 nm. Dissolve the aldehyde conjugate in water and lyophilize.

It is also possible to create new aldehyde groups in the polysaccharide chain by mild oxidation with periodic acid. After oxidation, the polysaccharide with the additional aldehyde groups is precipitated with alcohol and subjected to reductive amination as described above.

b) Addition of imine-forming compounds to β-glucans and mannans via the polysaccharide's —OH groups Another method to prepare glucan, mannan or similar polysaccharide derivatives of carbonyl carrying compounds, is to add the latter to the polysaccharides via the —OH groups. Because of the number of —OH per glycosyl residue, this method allows the preparation of conjugates with higher densities of carbonyl groups. A polysaccharide —OH group can be activated, and allowed to react with the carbonyl-carrying molecule. Alternatively, the carbonyl-carrying molecule is activated, and allowed to react with the polysaccharide —OH groups. See Scheme 2.

Direct conjugation of compounds carrying both carbonyl and hydroxyl groups to the polysaccharide —OH groups can be made with CDI. Ten gm of lyophilized glucan/mannan are dissolved in 100 ml of anhydrous DMSO or DMF plus pyridine (glycosyl residues ~55 mmolar). To the polysaccharide solution add a six-fold excess of CDI (0.3 moles of CDI=49 am), stir under nitrogen, and protect from moisture for 12 hours at 40° C. Under these reaction conditions most of the polysaccharide —OH groups will be activated with minimal cross-linking, with a concomitant production of imidazole. (If less activation is required, use lower amounts of CDI). The CDI-activated polysaccharide can be recovered by precipitation with 6–8 volumes of anhydrous acetone. Dissolve 1 gm of the CDI-activated polysaccharide in 50 ml of anhydrous DMF (add pyridine if needed) and add the carbonyl-carrying compound. To introduce 1 carbonyl group for each 10–20 glycosyl residues, add an amount of carbonyl component equivalent to about 6 to about 3 mmoles dissolved in DMF to the CDI-activated polysaccharide. Adjust pH to about 9 to about 10 with anhydrous triethylamine. React for about 36 hours at 40–60° C. with stirring and protection from moisture. The carbonyl compound-polysaccharide product is precipitated with 6–8 volumes of ethanol at 4° C. for about 36 hours. Wash the insoluble material with ethanol, and store in vacuum over a, strong desiccant. To remove the activated groups from the polysaccharide, dissolve the polysaccharide and store in 0.1 M Na acetate, pH 8.9, for 36 hours to hydrolyze all the unreacted imidazolyl carbamate, and to revert to the original —OH groups. Remove the imidazole formed during hydrolysis by dialysis, gel filtration, or by precipitating the derivatized polysaccharide with ethanol. After concentrating the product from an aqueous solution, lyophilize it.

Addition of compounds carrying both carbonyl and amino groups to polysaccharides' —OH can be made with N,N'-disuccinimidyl carbonate (DSC). Hydroxyl groups activated with DSC react almost exclusively with primary amines, but not with —OH groups. This avoids potential cross-linking of the polysaccharide. Unreacted DSC-activated —OH groups will revert by hydrolysis to their original state.

Six gm of the glucan/mannan polysaccharide (about 34 mmoles of glycosyl residues) are dissolved in 50–100 ml of acetonitrile, DMF, DMSO, pyridine, or mixtures thereof containing 9 gm of DSC (34 mmoles) (about 1 mole of DSC/mole of glycoside residue). During a period of 60 min. and with stirring at 50–80° C., add dropwise (under dry $N_2$) 50 ml of dry pyridine containing 8.6 ml (62 mmoles) of anhydrous triethylamine. Continue the reaction, under anhydrous conditions at 50–80° C. for another 4–6 hours. Depending on the reaction conditions and the polysaccharide, the preparation should have 0.1 to 1 activated —OH groups per glycosyl residue. Precipitate the DSC-activated polysaccharide by addition of about 8 volumes of anhydrous isopropanol and let stand at 40° C. for 24 hours protected from moisture. Collect the precipitated polysaccharide, resuspend it and wash with dry isopropanol. One gm of DSC-activated polysaccharide (~6 mmoles) dissolved in 10 ml of THF or DMF, alone or in combination with pyridine, is allowed to react with the selected amino/carbonyl-containing compound. The degree of conjugation will depend on the reactant concentrations as well as the reaction conditions.

To incorporate 0.1 carbonyl group per glycosyl residue (assuming a reaction efficacy of close to 100 percent), add with stirring 0.6 mmoles of the selected amino/carbonyl-containing compound, i.e., 0.105 gm of 7-amino-4-methylcoumarin (FW 175.2), or 0.080 gm of 4-aminoacetophenone (FW 135), to 1 gm of the DSC-activated polysaccharide. Add to the reaction anhydrous triethylamine in an amount equimolar to that of the carbonyl compound, i.e., 0.6 mmoles (80–85 μl). React for 1–2 hours at 50–80° C. At the end of the reaction recover the polysaccharide-derivative by precipitating it with 8 volumes of cold isopropanol for 24 hours. Collect the insoluble material, redissolve it in 0.1 M Na acetate pH 8.9, and let stand for 36 hours to hydrolyze unreacted imidazolyl carbamate groups. Precipitate with 6–8 volumes of cold ethanol or isopropanol for 24 hours to remove imidazole and other residual reactants. Dissolve the derivatized polysaccharide in water and lyophilize. Determine the degree of incorporation by measuring the absorbance at 260–280 nm. Confirm the presence of imine-forming carbonyl groups with Schiff reagent.

c) Addition of imine-forming compounds to pectic polysaccharides

Carboxyl groups from pectic polysaccharides (homogalacturonans, rhamnogalacturonans, arabinogalactans, arabans, or galactans), such as galacturonic, glucuronic, 3-deoxy-D-manno-octulosonic acid (Kdo), aceric, and other acids, are reactive groups that can be used to couple these polysaccharides to certain carbonyl-carrying compounds. Carboxyl groups can be coupled specifically to amines by using dicyclohexylcarbodiimide (DCC) and N-hydrosuccinimide (NHS). This reaction can be carried out in organic solvents such as dioxane, DMF, DMSO, acetonitrile, pyridine, or mixtures of the same. Carboxyl groups in polysaccharides can be determined indirectly, by using the DCC/NHS method to link a diamine, followed by determination of the bound amine with TNBS. The coupling can also be carried out in aqueous media using 1-ethyl-3-(3-dimethylaminopropyl) carbodiimide (EDC) in conjunction with N-hydroxysulfosuccinimide (sulfo-NHS), both of which are water-soluble.

In one example, to the pectic polysaccharide, dissolved in DMF or DMF-pyridine, add DCC and NHS, adjust the pH to between 8 and 9 with anhydrous triethylamine and stir overnight at 25° C. Remove the precipitated dicyclohexyl urea by filtration or centrifugation. The number of activated —COOH groups per glycosyl residue can be selected by i) using limiting amounts of DCC and NHS, or ii) controlling the activation time to form the intermediate. The activated polysaccharide is isolated prior to reacting with the amine-containing compound. Separation of the modified polysaccharide from DCC and NHS is accomplished by precipitation with 6 volumes of ethanol for 24 hours at 4° C., protected from moisture. To the ethanol-washed precipitate (activated polysaccharide) dissolved in DMF-pyridine, an excess (relative to the activated carboxyls) of amine-carbonyl containing compound, is added; the pH is adjusted to between 8 and 9 with anhydrous triethylamine, and reacted at 25° C. overnight with mixing. The derivatized pectic polysaccharide is precipitated with ethanol as previously described, washed with ethanol, and dissolved in 0.1–0.2 M ammonium acetate or bicarbonate. To increase its solubility in water, additional ammonium hydroxide can be added to bring the pH to about 8. Filter the solution to remove insoluble materials, and determine spectrophotometrically the degree of conjugation. The modified pectic polysaccharide containing carbonyl-carrying residues is lyophilized.

Use of the —COOH groups would enable the introduction of spacers between the glycosyl residues and the carbonyl compounds. For instance, compounds such as androsterone, prednisolone, pyridoxal, 4-hydroxyphenylacetaldehyde, 4'-hydroxybenzaldehyde, and others containing —OH groups can be activated with DSC, and subsequently reacted with the aminated polysaccharide, or with a diamine spacer. Hydroxyl groups activated with DSC react almost exclusively with primary amines, but not with —OH groups. See Scheme 3.

A hydroxylated carbonyl-containing compound (10 mmoles) is dissolved in anhydrous DMF, acetonitrile, or acetone containing 3 gm of DSC (11 mmoles) (~1 mole of DSC/mole of carbonyl compound). During a period of about 60 min., add dropwise (under dry $N_2$) with stirring at 50–80° C., 17 ml of dry pyridine containing 2.9 ml (20 mmoles) of anhydrous triethylamine. Continue the reaction under anhydrous conditions at 50–80° C. for another 4 to 6 hours to yield a preparation with about 1 activated —OH group per mole of compound. To incorporate a spacer, add an excess (50 mmoles) of lysine, 2,3 diamino-propionic acid, or similar spacer molecule, to the reaction followed by an amount of anhydrous triethylamine that is equimolar to that of the carbonyl compound, i.e., 10 mmoles (1.3 ml). Let react for 1–2 hours at 50–60° C. and recover product by adding water and extracting the aqueous solution with ethyl acetate, dichloromethane, or other appropriate solvent. The conjugated carbonyl-compound should partition into the organic phase. Check purity by TLC. Alternatively, the product is separated from the other reactants by silica gel chromatography. Collect the fractions with the carbonyl-spacer compound and evaporate to dryness.

Link the carbonyl-spacer compound to the pectic polysaccharides using the DCC/NHS method. To the polysaccharide dissolved in DMF or pyridine, add an amount of the carbonyl-spacer compound required to achieve the targeted degree of incorporation, such as 1 carbonyl group for every 10–20 glycosyl residues. Add the DCC/NHS and continue the reaction as previously described. Precipitate the modified pectic polysaccharide with ethanol. Wash the precipitate with alcohol, dissolve it in water, and precipitate it a second time with alcohol. Dissolve the precipitated material in 0.2 M ammonium bicarbonate or acetate, adjusting the pH to about 8–9 with ammonia. Filter out insoluble material and determine spectrophotometrically the incorporation of the carbonyl compound into the pectic polysaccharide. Confirm the presence of carbonyl groups qualitatively with Schiff reagent. Concentrate the aqueous solution, if needed, and lyophilize.

d) Addition of imine-forming compounds to chitin derivatives

Glucosamine amino groups from partially, or totally deacylated chitin (colloidal chitosan), glycol-chitin, and other water-soluble chitin derivatives, are reactive groups useful for coupling the polysaccharide to carbonyl carrying compounds. See Scheme 4.

Ten mmoles (1.6 gm) of CDI or N,N'-carbonyldiimidazole dissolved in 10 ml of anhydrous dioxane or acetone, are added with stirring in small aliquots to 10 mmoles of vanillin (1.5 gm), 4-hydroxybenzaldehyde (1.2 gm), 5-chloro-2-hydroxybenzaldehyde (1.6 gm), pyridoxal phosphate (2.47 gm), or other similar compounds, dissolved in 10 ml of dioxane or acetone, and allowed to react for 6–8 hours at 40° C. with mixing. Protect from atmospheric moisture. The reaction products are highly reactive intermediate imidazole carbamates which are formed with the —OH from the aromatic aldehyde derivatives, plus imidazole. This reaction mixture can be added to the chitosan or other chitin derivatives without prior isolation of the intermediate imidazole carbamate. The intermediate will couple with the polysaccharides' glucosamine amino groups to yield stable carbamate linkages. Isolate imidazole carbamate derivatives by chromatography, differential extractions, or other procedures.

Dissolve chitosan oligosaccharides or glycol chitin in a suitable anhydrous organic solvent, such as dimethylsulfoxide (DMSO), dioxane, or pyridine, and adjust the pH to about 9.5–10 with triethylamine. Add the amount of the carbonyl-containing carbamate intermediate required to yield a specified degree of incorporation (0.05 to 1 group/ glucosamine residue), and let react for about 12 to 18 hours at 40° C., protected from moisture. Add about 6–8 volumes of cold ethanol to the reaction and let stand at 4° C. for 24–48 hours to precipitate the polysaccharide-aromatic aldehyde conjugate. Redissolve the derivatized oligo- or polysaccharide in water, DMF, or DMSO, and re-precipitate again with 6–8 volumes of ethanol or other suitable solvent. Determine the efficacy of the coupling from the UV spectra. Dissolve the polysaccharide-aromatic aldehyde conjugate in water and lyophilize.

Carbonyl-carrying compounds containing carboxyl groups, such as 8,10-dioxoundecanoic and 4,6-dioxoheptanoic acids, can be linked to either chitosan oligosaccharides or aminated polysaccharides, using the DCC/NHS procedure described for pectic polysaccharides.

II. Preparation of Protein Antigen-Adjuvant Conjugates

Protein antigens can be conjugated to imine-forming carbonyl containing polysaccharide adjuvants by their side chains, such as amino, carboxyl, sulfhydryl, imidazole, and phenolic groups. Because conformational integrity of the protein antigen is not a requirement for induction of CTL response, the conjugation procedures can be carried-out under denaturing conditions. To minimize cross-linking between the adjuvant and the antigen, the number of reactive groups per mole of either (or both) antigen or adjuvant should be limited to a small number, typically between 1–50 antigen moieties per conjugate molecule, preferably less than 10 per molecule. Under these conditions, the conjugates formed will be prevalently of an antigen/adjuvant composition of ~1:1, without extensive cross-linking, although conjugates having antigen/adjuvant ratios of up to 50:1 (such as 20:1, 15:1, 10:1; 5:1 and 2:1) are within the scope of the invention. If needed, separation procedures, such as gel-permeation chromatography, will allow further purification of these preparations to obtain relatively homogeneous preparations.

a) Conjugation of protein antigens via their amino groups

A terminal or ε-amino group of a protein antigen can be linked covalently to polysaccharides by several procedures. If needed, the number of amino groups available for conjugation may be reduced by reversible trifluoroacetylation, or N-acylation with acid anhydrides (i.e., maleic, citraconic, and others), followed by controlled deacylation (see Glazer, A. N., et al., *Chemical Modification of Proteins*. In Work & Work (eds.) "Laboratory Techniques in Biochemistry and Molecular Biology", New York, American Elsevier). The N-acylation, which is stable at a pH greater than 8, can be reversed reproducibly by exposure to pH less than 4 at temperatures between 4° C. and 40° C. (Marciani et al., *Protein Purification: Micro to Macro*, Alan R. Liss, New York; and U.S. Pat. No. 4,743,362 (1987)).

Protein preparations having a specific number of free amino groups can be prepared by the following procedure. After modification of all the protein amino groups by reversible acylation, dialyze against a volatile buffer (ammonium carbonate) pH 8–9, and lyophilize. Deacylate a certain number of the amino groups by treatment at a pH less than 4 (at a specified temperature and time), and stop the deacylation process by bringing the pH of the reaction to a pH greater than 8. See Scheme 5. Use of volatile buffers allows direct lyophilization of the reaction mixture.

1a) Proteins conjugated via their —NH$_2$ groups to the —OH groups of polysaccharides using DSC Prepare the carbonyl compound-containing glucan by linking carbonyl-containing compounds to the polysaccharide —OH groups, using the procedure described in Section 1-b, Scheme 2, above. Dissolve 0.6 gm of the carbonyl compound-containing polysaccharide (~3.4 mmoles of glycosyl residues) in 5–10 ml of DMF, acetonitrile, DMSO, pyridine, or mixtures of the same containing 0.9 gm. of DSC (0.34 to 3.4 mmoles) (~0.1 to 1 mole of DSC/mole of glycoside residue). During a period of 0.5 to 1 hour add dropwise (under dry N$_2$) with stirring at 40° C., 5 ml of dry pyridine containing 0.9 ml (6.2 mmoles) of anhydrous triethylamine. Continue the reaction under anhydrous conditions at 35° C. for another 0 to 4 hours. The preparation of carbonyl-containing polysaccharide should have 0.01 to 1 activated —OH groups per glycosyl residue. Precipitate the activated polysaccharide by addition of 8 volumes of anhydrous isopropanol and let stand at 4° C. for 24 hours protected from moisture. Collect the precipitated polysaccharide and wash with dry isopropanol. Dissolve the activated polysaccharide in THF or DMF, alone or with pyridine, to react with the protein antigen. The degree of conjugation will depend on the reactants concentrations as well as the reaction conditions.

For example, Scheme 6 illustrates the preparation of an approximately 1:1 conjugate of bovine serum albumin (BSA, M. W. 68,000) and a carbonyl-containing glucan (average M. W. about 10,000). To 0.1 gm (10 μmoles) of the carbonyl-containing DSC-activated glucan (having 2–5 activated —OH per mole) and dissolved in 2 ml of pyridine/DMF or similar solvent, add 0.7 gm (10 μmoles) of a partially deblocked citraconilated BSA (1–4 —NH$_2$ groups/mole) dissolved in 10 ml of DMF or DMF/pyridine. Add to the reaction an amount of anhydrous triethylamine that is equimolar to that of the protein, i.e., 10 μmoles (1–2 μl), and react for 2–4 hours at 25° C. Separate the protein-polysaccharide conjugate from the unreacted materials by gel-filtration, ion-exchange, or affinity chromatography, or precipitation with either ammonium sulfate or ethanol. The precipitated protein-polysaccharide conjugate is collected, and dissolved in pyridine/acetic acid buffer, pH ~4, to deblock all the residual citraconilated amino groups. Remove by-products and exchange buffers by dialysis or gel filtration, and lyophilize. Determine the approximate molecular weight of the conjugate, and its degree of conjugation from the protein and polysaccharide concentrations.

2a) Proteins conjugated by their amino groups to the carboxyl groups of acidic polysaccharides, such as pectic polysaccharides, using the DCC/NHS procedure To limit the cross-linking between the protein antigen and the aldehyde-containing pectic polysaccharide, the protein amino groups can be blocked to a large extent by the N-acylation procedure described above. Subsequently, after the conjugation the acylated amino groups can be deblocked by exposure to a pH less than 5.

b) Conjugation of protein antigens via their sulfhydryl groups

Sulfhydryl groups are highly reactive groups with a limited distribution in =proteins. These characteristics make them suitable for conjugation of protein antigens to carbonyl-containing polysaccharides. Cross-linking of protein antigens to an aminated-polysaccharide derivatized with carbonyl compounds can be performed with heterobifunctional cross-linkers, such as succinimidyl 4-(p-maleimidophenyl)butyrate (SMPB), 4-(4-N-maleimidophenyl)butyric acid hydrazide hydrochloride (MPBH), maleimidobenzoyl-N-hydroxysuccinimide ester (MBS), and others (Pierce). See Scheme 7. In general, these cross-linking agents react first with an amino or a carbonyl group from the polysaccharide, and subsequently with a sulfhydryl group from the protein antigen. The linkage formed by these agents are non-cleavable, and frequently poorly immunogenic. Following is procedure to prepare protein-polysaccharide conjugates having 1–2 moles of protein per mole of glucan or mannan of M. W. of about 100,000, or about 555 glycosyl residues.

Six gm (60 $\mu$moles) of a glucan/mannan polysaccharide of M. W approximately 100,000 (~34 mmoles of glycosyl residues) are dissolved in 50–100 ml of acetonitrile, DMF, DMSO, pyridine, or mixture of the same containing 9 gm of DSC (34 mmoles), or ~1 mole of DSC/mole of glycoside residue. During a period of 60 min. add dropwise (under dry $N_2$) with stirring at 50–80° C., 50 ml of dry pyridine containing 8.6 ml (62 mmoles) of anhydrous triethylamine. Continue the reaction under anhydrous conditions at 50–80° C. for another 6–8 hours. Depending on the reaction conditions and the polysaccharide, the preparation should have 0.5 to 1 activated —OH groups per glycosyl residue. Precipitate the activated polysaccharide by addition of about 8 volumes of dry isopropanol, protect from humidity and let stand at 4° C. for 24 hours. Collect the precipitated polysaccharide, resuspend it and wash with dry isopropanol. Hydroxyl groups activated with DSC react almost exclusively with primary amines, but not with —OH groups.

One gm of the DSC-activated polysaccharide (5.5 mmoles of monomeric glucoside), having 0.5–1.0 activated —OH groups/glycosyl residue, and dissolved in 10–20 ml of THF or DMF alone or with pyridine, is allowed to react with 0.55 mmoles of a diamine, such as ethylenediamine, 2,3-diaminopropionic acid, or a similar diamine. Add to the reaction anhydrous triethylamine in an amount equimolar to that of the anhydrous diamine compound, i.e., 0.6 mmoles (~80 $\mu$l). React for 4–6 hours at 50–80° C. to produce a polysaccharide-derivative, containing ~40–50 —$NH_2$ per ~500 glycosyl residues. Dilute 10-fold with aqueous 0.1 M sodium acetate, pH ~8.9, 0.1 M potassium acetate, pH ~9.5, or similar solutions with pH 8.5–9.5, and maintain at 35–40° C. for 8–12 hours to hydrolyze the residual DSC-activated —OH groups. (Do not use buffer solutions containing ammonia, primary or secondary amines, and select cations that are soluble in alcohol to facilitate their removal). Remove water by rotary evaporation under reduced pressure, and precipitate and wash the aminated polysaccharide with isopropanol.

To 1 gm of aminated polysaccharide (~0.5 mmoles —$NH_2$) dissolved in 10–20 ml of anhydrous pyridine, add ~0.4 mmoles of 8,10-dioxoundecanoic acid, 4,6-dioxoundecanoic acid, 4,6-dioxoheptanoic acid, 3-carboxybenzaldehyde or 4-carboxybenzaldehyde, dissolved in 5–10 ml pyridine. (The amount of carbonyl compound added is equivalent to 80% of the total number of free amine groups on the polysaccharide). To this mixture, add 105 mg (0.5 mmoles) of DCC and 47 mg (0.4 mmoles) of NHS, and let react with mixing for 6 hours or until the reaction is completed. [Completion of the reaction, as well as the residual free —$NH_2$, can be determined by the TNBS method].

After completing the addition of carboxylated compound to the aminated polysaccharide, add to the reaction mixture 0.1 mmoles (28 mg) of the hetero-bifunctional cross-linking agent N-($\gamma$-maleimidobutyryloxy)succinimide ester (GMBS) dissolved in pyridine or DMF, and let react for 2–4 hours. Completion of the reaction can be determined with the TNBS method. Separate the polysaccharide-derivative (containing 1 to 10 maleimide groups per ~500 glycosyl residues) from the other reactants by i) precipitation with isopropanol, ii) gel filtration or iii) diafiltration, with aqueous solvents. If gel filtration or diafiltration are used, concentrate the aqueous solution, and lyophilize it.

The protein antigen should have available free —SH groups to react with the polysaccharide maleimide groups to form stable thioether linkages. (If needed, treat the protein with a reducing agent, i.e., 2-mercaptoethanol, to regenerate the —SH groups, remove the agent by dialysis or gel filtration, and lyophilize the reduced protein). The reaction can be carried out in aqueous organic solvents. To 10 $\mu$moles (~1 gm of the activated polysaccharide M. W. 100,000) dissolved in 20 ml of pyridine, DMF, or mixtures of both solvents, add 10 $\mu$moles of protein containing a limited number of —SH groups per molecule, and let react for several hours. Stop the reaction by: adding an excess of $\beta$-mercaptoethanol to the reaction mixture and reacting for 1 hour. Separate the protein:polysaccharide derivative conjugate from solvents and other reactants by diafiltration or gel filtration. The conjugate can be purified further by different chromatographic methods such as ion-exchange and gel permeation chromatography. Alternatively, the conjugate can be purified by precipitation with salts, or organic solvents. Analyze the conjugate's composition by HPLC, polyacrylamide electrophoresis, or other appropriate methods.

Pharmaceutical and Veterinary Compositions and Methods of Using

Recent studies (Rhodes, J., Immunology Today 17:436 (1996)) have shown that exogenous Schiff-base-forming compounds can substitute for natural donors of carbonyl groups and provide a costimulatory signal to CD4 T helper (Th) cells. In a related study (Zheng, B. et al., Science, 256:1560 (1992)), treatment of APCs with galactose oxidase to form new aldehyde groups resulted in an adjuvant effect when administered with an antigen to mice.

These findings stress the role of Schiff-base forming compounds as stimulators of the immune system. During interaction between an APC and Th-cell there is a transient formation of a Schiff-base between a specialized APC's carbonyl groups and the Th-cell's amino groups located on still undefined cell-surface-receptors. Consequences of the Schiff-base formation are: the biasing of the immune system toward a Th1-type response with an increase in the IL-2 and IFN-$\gamma$ production in Th-cells, and the enhancement of the CTL response. Schiff base forming compounds appear to work by bypassing the co-stimulatory pathway involving the CD-28 receptor on Th-cells and the B7-1 receptor present on APCs.

There are a variety of circumstances in which the immune system may be defective or deficient. For example immune system deficiency is common in immature or premature infants (neonates). It may also result from suppression by certain drugs which may be deliberate e.g. as a side-effect of cancer chemotherapy. Disordered growth of one or more constituent parts of the immune system, e.g. as in certain forms of cancer, may also result in immunodeficiency. Immune deficiency can also be caused by viral infections, including human immunodeficiency virus (HIV).

A further aspect of the present invention provides for the use, as a combined vaccine-adjuvant, of a conjugate of the present invention, for example a compound of Formula I or a physiologically acceptable salt thereof. A vaccine may therefore be prepared by formulating a conjugate of the present invention.

Compounds of the present invention maybe administered to a human recipient by a route selected from oral, parenteral (including subcutaneous, intradermal, intramuscular and intravenous), rectal and inhalation. The size of an effective dose of a compound will depend upon a number of factors including the identity of the recipient, the type of immunopotentiation involved, the severity of the condition to be treated and the route of administration, and will ultimately be at the discretion of the attendant physician.

The effective dose will generally be in the range of 0.03 to 250 mg per individual, and most preferably between about 0.05 to about 100 mg per dose. Immune stimulators are preferably administered only once or twice a week, and in some cases, less frequently. Frequency and length of treatment vary among species and individuals.

While it is possible for the compounds of the present invention to be administered as the raw chemical it is preferable to present them as a pharmaceutical formulation preparation. The formulations of the present invention comprise a compound of the present invention, together with one or more acceptable carriers therefor and optionally other therapeutic ingredients. The carrier(s) must be acceptable in the sense of being compatible with the other ingredients of the formulation and not deleterious to the recipient thereof.

Immune adjuvants are compounds which, when administered to an individual or tested in vitro, increase the immune response to an antigen in a subject or in a test system to which the antigen is administered. Some antigens are weakly immunogenic when administered alone or are toxic to a subject at concentrations that evoke useful immune responses in a subject. An immune adjuvant can enhance the immune response of the subject to the antigen by making the antigen more strongly immunogenic. The adjuvant effect can also result in the ability to administer a lower dose of antigen to achieve a useful immune response in a subject.

The immunogen-inducing activity of compounds and compositions of the present invention can be determined by a number of known methods. The increase in titer of antibody against a particular antigen upon administration of a composition of the present invention can be used to measure immunogenic activity. (Dalsgaard, K. *Acta Veterinia Scandinavica* 69:1–40 (1978)). One method requires injecting CD-1 mice intradermally with a test composition that includes one or more exogenous antigens. Sera is harvested from mice two weeks later and tested by ELISA for anti-immunogen antibody.

Poorly antigenic proteins, covalently bound to modified polysaccharide adjuvants, are used to show an immunogenicity enhancement. For this purpose, two poorly immunogen proteins, chicken lysozyme and rabbit actin, have been selected. Mice are immunized either with the selected conjugate plus different amounts of the free adjuvant, or with the free antigen plus the adjuvant. Booster immunizations using the same formulations are given four and eight weeks after the first immunization. The titers for IgG and IgG subclasses, stimulated by the antigen-adjuvant conjugates or by the free antigen plus adjuvant, are determined by ELISA at 4, 8, and 12 weeks after the first immunization.

The antigen-adjuvant conjugate effects on T-cell immunity are determined by using an in vitro T-cell proliferation assay. Spleen cells from animals sacrificed 4 weeks after the third immunization are used in the assay. In triplicate, $4 \times 10^5$ cells are cultured with 0.2 ml medium containing 0. 2 or 10 $\mu$g per ml of OVA. After 2–3 days in culture, cells are pulsed with 1 $\mu$Ci of $^3$H-thymidine for 12 hours. The cells are harvested and the amount of incorporated $^3$H-thymidine determined by liquid scintillation counting. The cell proliferation is expressed counts per minute (cpm) in stimulated cells minus the cpm in the controls.

Compositions of the invention are useful as vaccines to induce active immunity towards antigens in subjects. Any animal that may experience the beneficial effects of the compositions of the present invention within the scope of subjects that maybe treated. The subjects are preferably mammals, and more preferably humans.

Conjugates of the present invention can be employed alone, or alternatively, can be administered together with other adjuvants. Such adjuvants useful with the present invention include oil adjuvants (for example, Freund's Complete and Incomplete), saponins, modified saponins, liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, lipid A, wax D from *Mycobacterium tuberculosis*, as well as substances found in *Corynebacterium parvum*, *Bordetella pertussis*, and members of the genus Brucella), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. When obtained from recombinant sources, the non-saponin adjuvant may comprise a protein fragment comprising at least the immunogenic portion of the molecule. Other known immunogenic macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3,3'-dicarboxylic acid and 4-nitro-2-aminobenzoic acid (See Sela, M., *Science* 166:1365–1374 (1969)) or glycolipids, lipids or carbohydrates.

The conjugates of the present invention exhibit adjuvant effects when administered over a wide range of dosages and a wide range of ratios to one or more particular antigens being administered. The conjugates can be administered either individually or admixed with other substantially pure adjuvants to achieve an enhancement of immune response to an antigen.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered. In general, the polysaccharide adjuvant-antigen conjugates maybe administered over a wide range of dosages and a wide range of ratios to the antigen being administered. The initial dose may be followed up with a booster dosage after a period of about four weeks to enhance the immunogenic response. Further booster dosages may also be administered. The conjugates of the present invention may be employed in such forms as capsules, liquid solutions, emulsions, suspensions or elixirs for oral administration, or sterile liquid forms such as solutions, emulsions or suspensions. Any inert carrier is preferably used, such as saline, or phosphate-buffered saline, or any such carrier in which the compounds used in the method of the present invention have suitable solubility properties for use in the methods of the present invention.

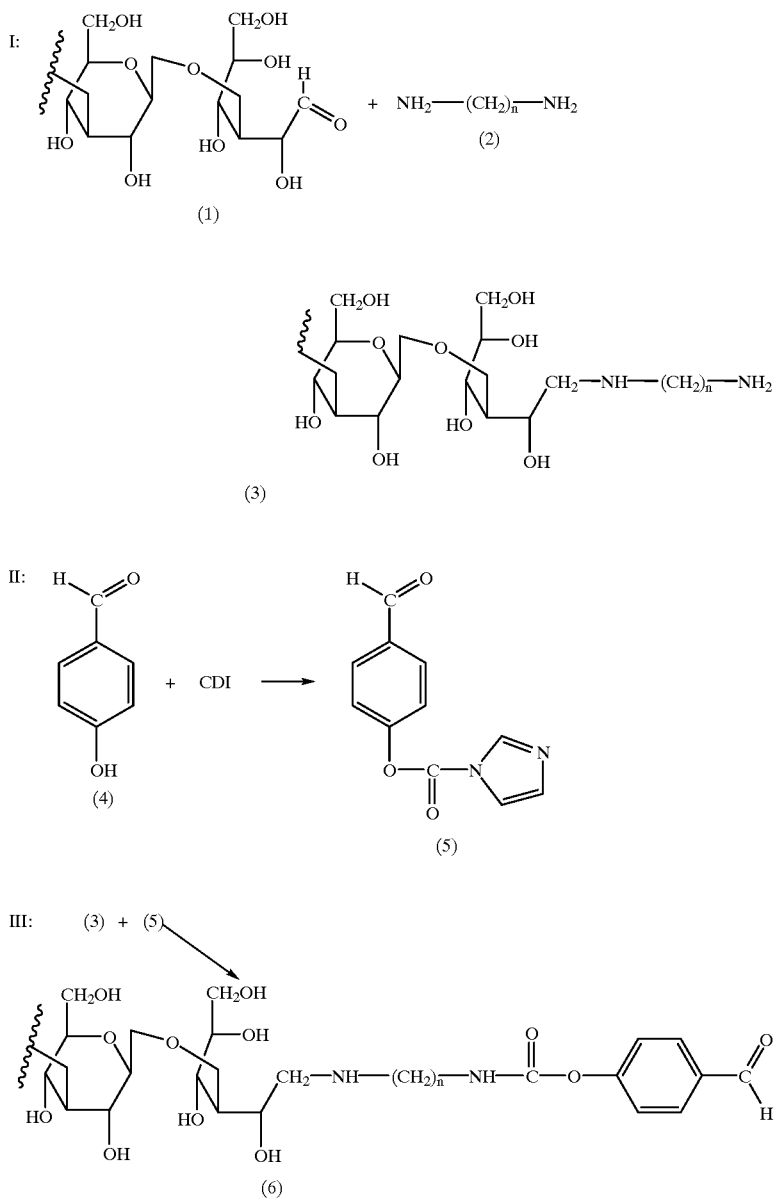

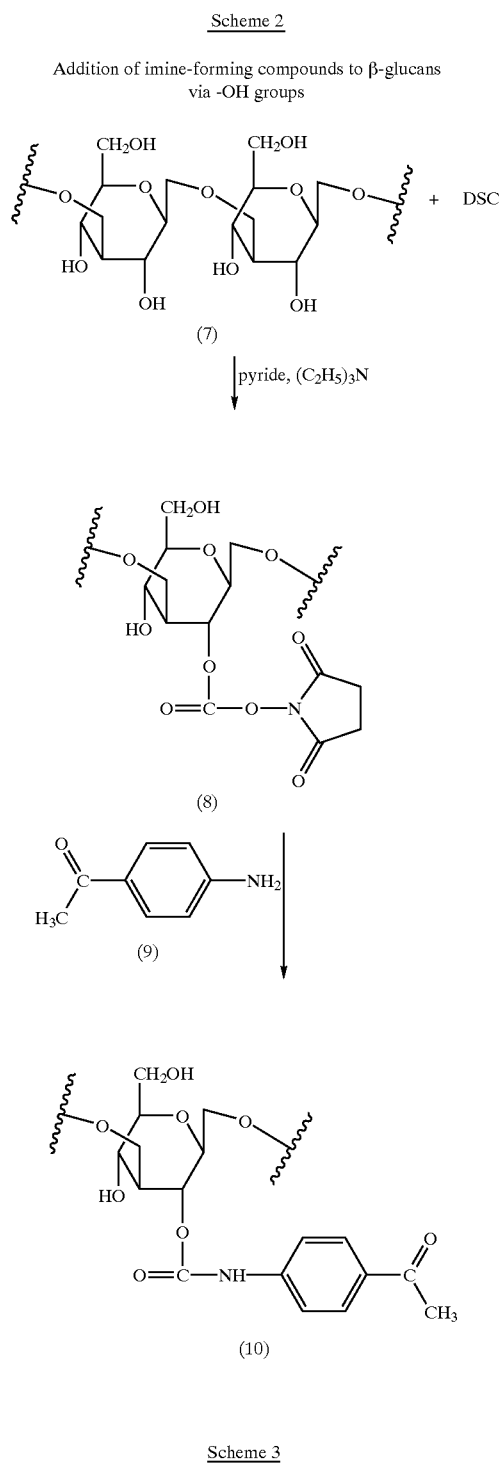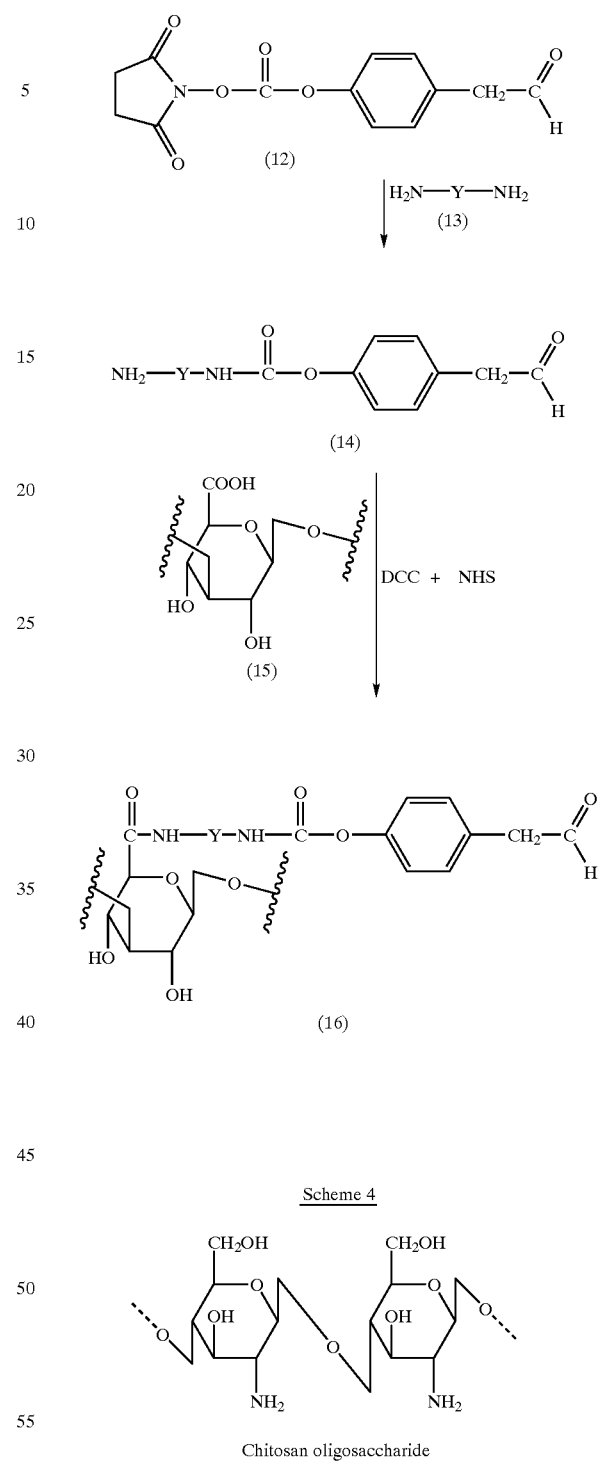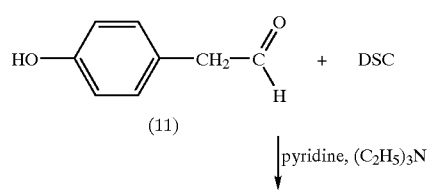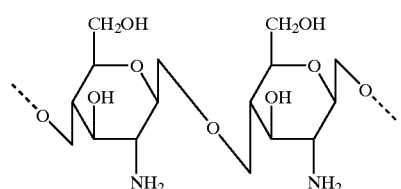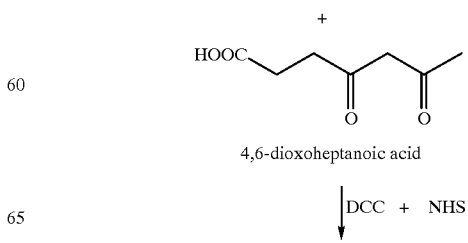

31
-continued
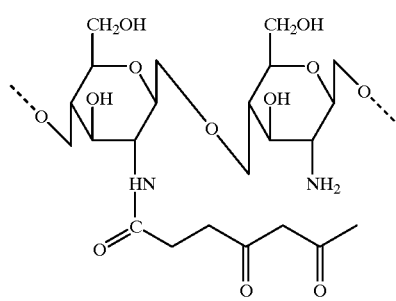
Scheme 5
32
-continued
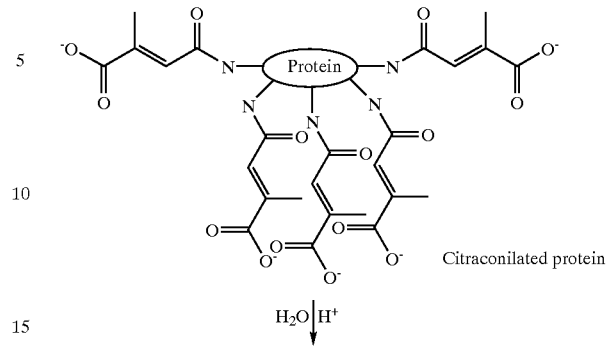
Citraconilated protein
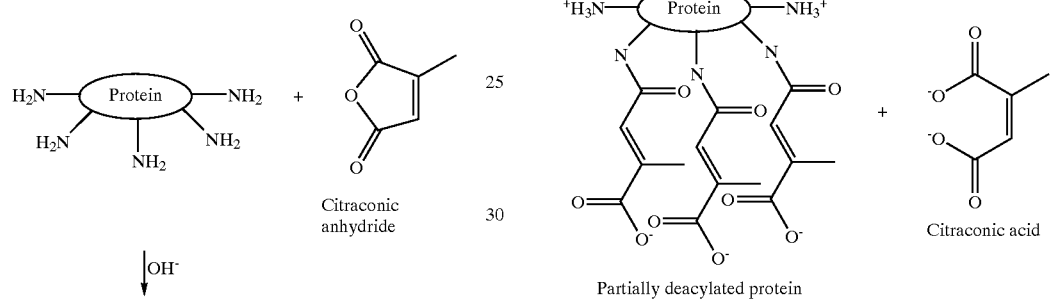
Partially deacylated protein
Scheme 6
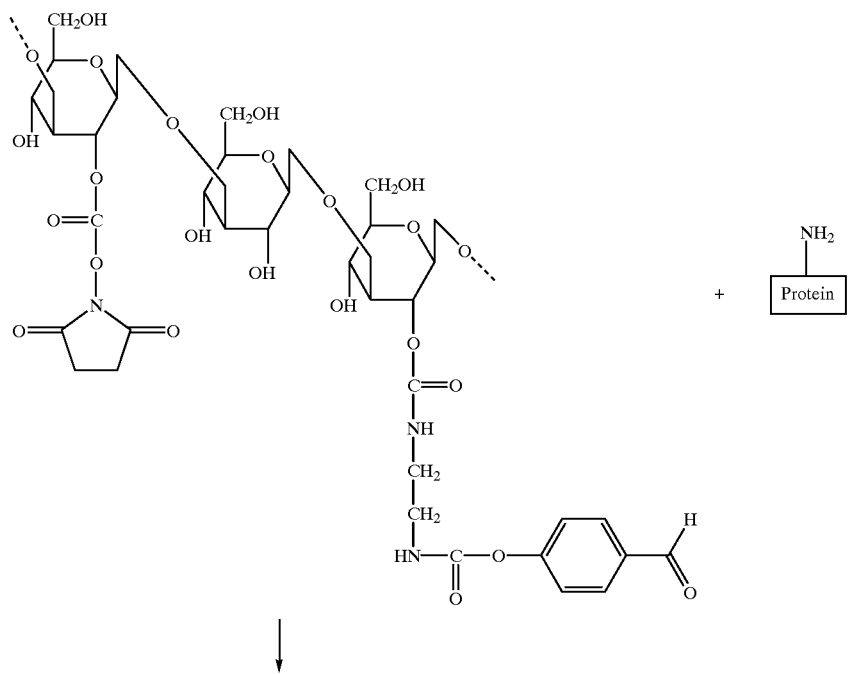

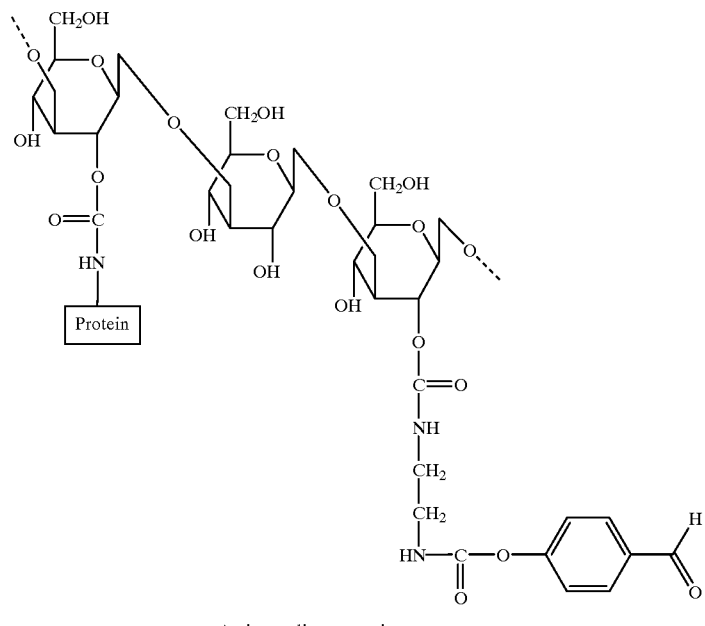
Antigen-adjuvant conjugate
Scheme 7
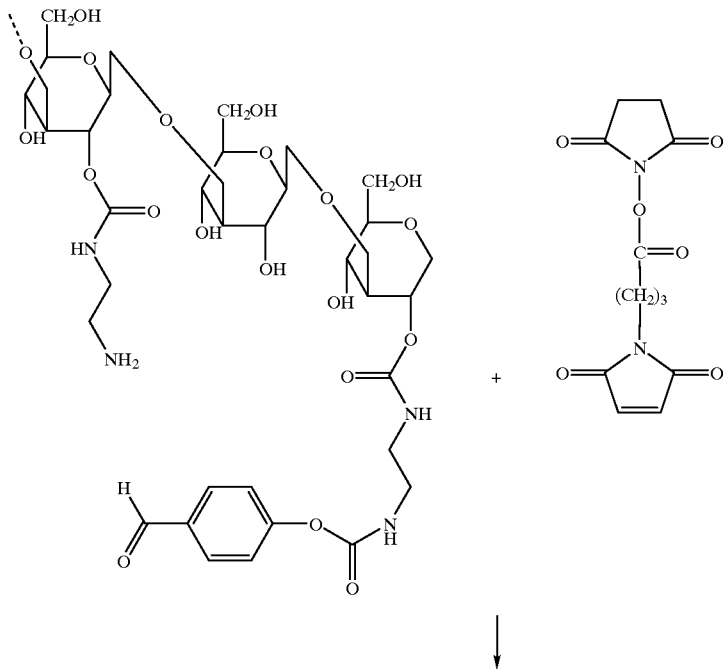

-continued

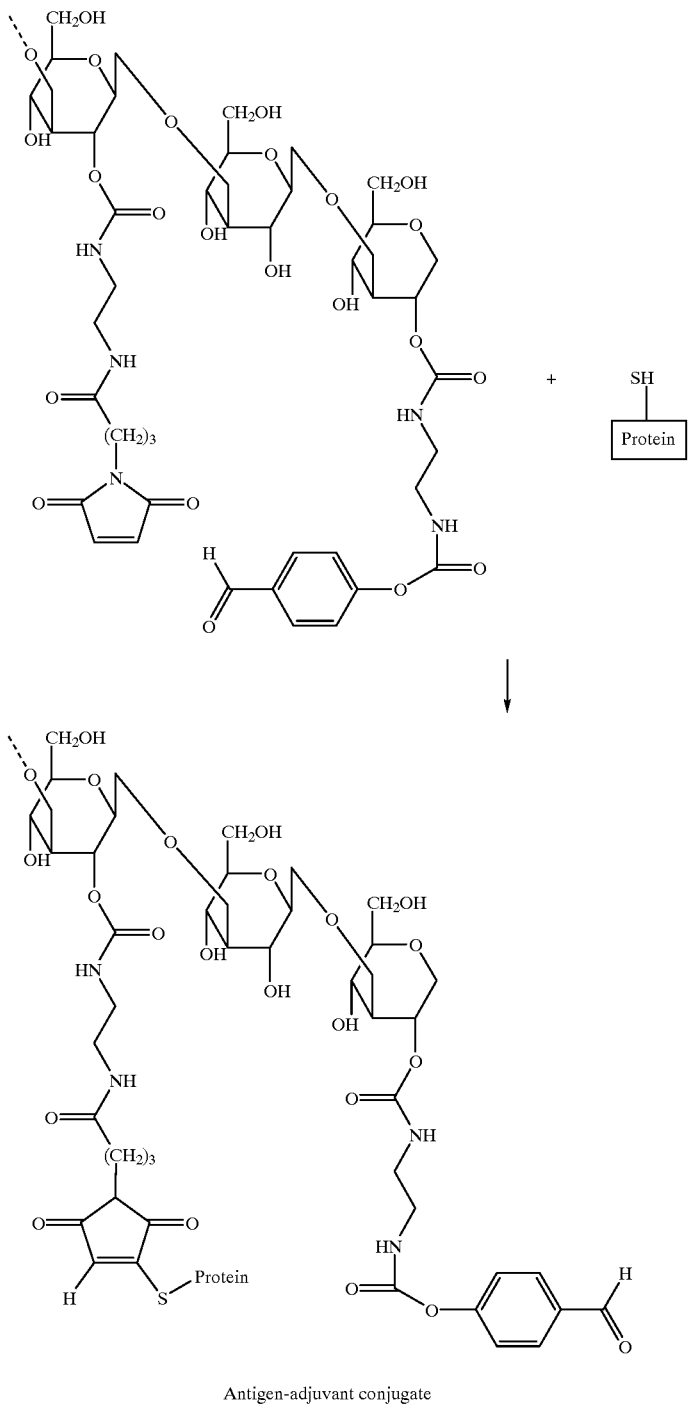

Antigen-adjuvant conjugate

Having now fully described this invention, it will be understood to those of ordinary skill in the art that the same can be performed within a wide and equivalent range of conditions, formulations, and other parameters without affecting the scope of the invention or any embodiment thereof. All patents and publications cited

What is claimed is:

1. A polysaccharide adjuvant-protein antigen conjugate, wherein said conjugate is represented by the formula:

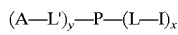

or pharmaceutically acceptable salts thereof, where

P is a polysaccharide which will bind to the cell surface of an Antigen Presenting Cell;

each L' is the same or different and is a covalent bond, or a bifunctional linking molecule;

A is a protein or peptide antigen which will elicit an immunogenic response when covalently attached to a polysaccharide backbone, and wherein when y is greater than 1, each A can be the same or different protein or peptide;

each L is the same or different and is a covalent bond, or a bifunctional linking molecule; and I is an compound having a stable carbonyl group capable of reacting with an amino group on an Antigen Presenting Cell to form an imine or Schiff's base, said compound having (a) a ketone or aldehyde functionality; and (b) a second functional group which reacts with a complementary functional group present on said polysaccharide or said bifunctional linking molecule, if present, and wherein when x is greater than 1, each I can be the same or different;

x is from 1 to 100 units per 100 glycoside residues; and y is from 1 to about 20 units per 100 glycoside residues.

2. The conjugate of claim 1, wherein said imine-forming compound is selected from the group consisting of aromatic aldehydes, aromatic ketones, cycloalkyl aldehydes, cycloalkyl ketones, cycloalkenyl aldehydes, cycloalkenyl ketones, heterocyclic aldehydes, heterocyclic ketones, heteroaromatic ketones, heteroaromatic aldehydes, alkyl aldehydes, alkyl ketones, alkenyl aldehydes, alkenyl ketones, and mixtures thereof.

3. The conjugate of claim 1, wherein said imine-forming compound is bound to said polysaccharide via a direct covalent bond.

4. The conjugate of claim 1, wherein said imine-forming compound is bound to said polysaccharide via a bifunctional linker molecule.

5. The conjugate of claim 1, wherein said imine-forming compound is selected from the group consisting of mono- and di-substituted $C_{6-10}$ arylaldehydes, $C_{6-10}$ aryl($C_{1-4}$) alkylaldehydes, hydroxy-substituted $C_{1-4}$alkyl($C_{6-10}$)aryl ketones, hydroxy-substituted $C_{6-10}$ aryl ketones, and mixtures thereof.

6. The conjugate of claim 5, wherein said imine-forming compound is one of phenyl or naphthyl substituted by a formyl or formyl($C_{1-4}$)alkyl substituent, and optionally including one or two additional substituents independently selected from the group consisting of halo, hydroxy, $C_{1-4}$ alkyl, $C_{1-4}$ alkoxy, trifluoromethyl, and benzyloxy.

7. The conjugate of claim 6, wherein said imine-forming compound is one of benzaldehyde and naphthaldehyde, substituted by one or two of hydroxy and halo.

8. The conjugate of claim 7, wherein said imine-forming compound is one of 2,3-dihydroxybenzaldehyde, 2,4-dihydroxybenzaldehyde, 2,5-dihydroxybenzaldehyde, 3,4-dihydroxybenzaldehyde, 5-chloro-2-hydroxybenzaldehyde, vanillin, ethyl vanillin, naringenin, 3-hydroxybenzaldehyde, 4-hydroxybenzaldehyde, 4-hydroxyphenylacetaldehyde, 2-hydroxyacetophenone, 3-hydroxyacetophenone, 4-hydroxyacetophenone, 6-hydroxy-1,2-naphthoquinone, 4,6-dioxoheptanoic acid or 8,10-dioxoundecanoic acid.

9. The conjugate of claim 1, wherein said imine-forming compound is selected from the group consisting of $C_{4-10}$ alkylaldehydes, $C_{4-10}$ alkenylaldehydes, $C_{4-10}$ alkylketones, $C_{4-10}$ alkenylketones, and mixtures thereof, all of which are substituted by one or two of amino, hydroxy or a combination thereof.

10. The conjugate of claim 1, wherein said imine-forming compound is selected from the group consisting of heteroaryl aldehydes and heteroaryl ketones.

11. The conjugate of claim 10, wherein said imine-forming compound is one of thiophene, furan, benzothiophene, benzofuran, pyridine, quinoline, pyridazine, pyrimidine, pyrazole, imidazole, 1,2,3-triazole, 1,2,4-triazole, isoxazole, or oxazole, each having a keto, formyl or formyl($C_{1-4}$)alkyl substituent, and optionally including an additional halo or hydroxy substituent.

12. The conjugate of claim 11, wherein said imine-forming compound is one of pyridoxal, 2-thiophenecarboxaldehyde, and 3-thiophenecarboxaldehyde.

13. The conjugate of claim 1, wherein said polysaccharide comprises a minimum of seven glycosyl residues.

14. The conjugate of claim 13, wherein said polysaccharide is selected from the group consisting of β-glucans; mannans; pectic polysaccharides; chitin; deacetylated chitin; glycol chitin; carboxymethyl chitin; hydrolyzed chitin; murein; bacterial fructans; xanthans; bacterial heteropolysaccharides; fungal pullulan; and esters, sulfonates, sulfates, phosphates, ethers, and cross-linked derivatives thereof.

15. The conjugate of claim 14, wherein said polysaccharide is selected from the group consisting of β-glucans; mannans; pectic polysaccharides; and 2-acetamido glucan polysaccharides.

16. The conjugate of claim 15 wherein said polysaccharide is a β-glucan having a backbone chain of (1→3)-linked β-D-glucopyranosyl units and which has β-D-glucopyranosyl units attached by (1→6) linkages, and a molecular weight of between about 5,000 to about 500,000, and wherein said β-glucan is optionally modified by the addition of one or more anionic, cationic or non-ionic groups.

17. The conjugate of claim 15, wherein said polysaccharide is a β-mannan comprising (1→4) polymannose having a terminus reducing mannosyl residue, or the acetylation product thereof.

18. The conjugate of claim 15, wherein said polysaccharide is a pectic polysaccharide selected from the group consisting of homogalacturonans, rhamnogalacturonans, arabinans, galactans, and arabinogalactans.

19. The conjugate of claim 1, wherein said protein antigen is derived from a virus, bacteria, protozoan, fungi, or mixtures thereof.

20. The conjugate of claim 19, wherein said protein antigen is derived from a virus, or bacteria that cause influenza, feline leukemia, feline immunodeficiency, HIV-1, HIV-2, rabies, measles, hepatitis B, hoof and mouth disease, anthrax, diphtheria, Lyme disease, tuberculosis, or mixtures thereof.

21. The conjugate of claim 1, wherein said protein antigen is bound to said polysaccharide via a direct covalent bond.

22. The conjugate of claim 1, wherein said protein antigen is bound to said polysaccharide via a residue of a bifunctional linker molecule.

23. The conjugate of claim 1, wherein said protein antigen is selected from the group consisting of carcinoembryonic antigen, prostate-specific membrane antigen, prostate specific antigen, protein MZ2-E, polymorphic epithelial mucin, folate-binding-protein LK26, an epitope of carcinoembryonic antigen, an epitope of prostate-specific membrane antigen, an epitope of prostate specific antigen, an epitope of protein MZ2-E, an epitope of polymorphic epithelial mucin, an epitope of folate-binding-protein LK26 and mixtures thereof.

24. The conjugate of claim 1, wherein said bifunctional linking molecule is a residue of a compound selected from the group consisting of succinimidyl 4-(p-maleimidophenyl) butyrate, 4-(4-N-maleimidophenyl)butyric acid hydrazide hydrochloride, and maleimidobenzoyl-N-hydroxysuccinimide ester.

25. The conjugate of claim 1, wherein said bifunctional linking molecule is a residue of a compound selected from the group consisting of:

$H_2N$—$(CH_2)_r$—$NH_2$, where r is from 2 to 12;

HO—$(CH_2)_r$—$NH_2$, where r is from 2 to 12;

HS—$(CH_2)_r$—$NH_2$, where r is from 2 to 12;

amino acids that are optionally carboxy-protected; and

H—$(O-CH_2-CH_2)_n$—OH, where n is 1–4.

26. The conjugate of claim 1, wherein said bifunctional linking molecule is a residue of a compound selected from the group consisting of ethylenediamine, 1,4-butanediamine, spermidine, 2,4-diaminobutyric acid, lysine, β-alanine, γ-aminobutyric acid, dialanine, trialanine, 3,3'-diaminodipropylamine, diaminopropionic acid, N-(2-aminoethyl)-1,3-propanediamine, and 2-(4-aminophenyl) ethylamine.

27. The conjugate of claim 1, wherein said bifunctional linking molecule is selected from the group consisting of:

—NH—$(CH_2)_r$—NH—, where r is from 2–5,

—O—$(CH_2)_r$—NH—, where r is from 2–5,

—NH—$CH_2$—C(O)—,

—O—$CH_2$—$CH_2$—O—$CH_2$—$CH_2$—O—,

—NH—NH—C(O)—$CH_2$—,

—NH—$C(CH_3)_2$—C(O)—,

—S—$(CH_2)_r$—C(O)—, where r is from 1–5,

—S—$(CH_2)_r$—NH—, where r is from 2–5,

—S—$(CH_2)_r$—O—, where r is from 1–5,

—S—$(CH_2)$—$CH(NH_2)$—C(O)—,

—S—$(CH_2)$—CH(COOH)—NH—,

—O—$CH_2$—CH(OH)—$CH_2$—S—$CH(CO_2H)$—NH—,

—O—$CH_2$—CH(OH)—$CH_2$—S—$CH(NH_2)$—C(O)—,

—O—$CH_2$—CH(OH)—$CH_2$—S—$CH_2$—$CH_2$—NH—,

—S—$CH_2$—C(O)—NH—$CH_2$—$CH_2$—NH—, and

—NH—O—C(O)—$CH_2$—$CH_2$—O—$P(O_2H)$—.

28. A pharmaceutical composition, comprising:

(a) a conjugate of claim 1, and (b) a pharmaceutically acceptable carrier or diluent.

29. A method of enhancing an immune response in an animal, comprising administering, to an animal in need of such enhancement, a composition of claim 28 in an amount effective to enhance the immune response of said animal.

30. A polysaccharide adjuvant-antigen conjugate, comprising:

(i) a polysaccharide having a minimum of seven glycosyl residues, said polysaccharide selected from the group consisting of a β-glucan; a mannan; a pectic polysaccharide; chitin; deacetylated chitin; glycol chitin; carboxymethyl chitin; hydrolyzed chitin; murein; a bacterial fructan; a xanthan; a bacterial heteropolysaccharide; fungal pullulan; and esters, sulfonates, sulfates, phosphates, ethers, and cross-linked derivatives thereof;

(ii) one or more molecules selected from the group consisting of aromatic aldehydes, aromatic ketones, cycloalkyl aldehydes, cycloalkyl ketones, cycloalkenyl aldehydes, cycloalkenyl ketones, heterocyclic aldehydes, heterocyclic ketones, heteroaromatic ketones, heteroaromatic aldehydes, alkyl aldehydes, alkyl ketones, alkenyl aldehydes, alkenyl ketones, and mixtures thereof;

(iii) a protein antigen capable of eliciting an immune response when covalently attached to said polysaccharide;

wherein one or more molecules (ii) are attached to the polysaccharide (i) through a direct covalent bond or covalently via a bifunctional linker in a manner that keeps the carbonyl group of molecule (ii) intact; and wherein said protein antigen (iii) are attached to the polysaccharide (i) through a direct covalent bond or covalently via a bifunctional linker.

31. The polysaccharide adjuvant-antigen conjugate of claim 30, wherein said protein antigen is selected from the group consisting of carcinoembryonic antigen, prostate-specific membrane antigen, prostate specific antigen, protein MZ2-E, polymorphic epithelial mucin, folate-binding-protein LK26, an epitope of carcinoembryonic antigen, an epitope of prostate-specific membrane antigen, an epitope of prostate specific antigen, an epitope of protein MZ2-E, an epitope of polymorphic epithelial mucin, an epitope of folate-binding-protein LK26 and mixtures thereof.

* * * * *